United States Patent
Brown

(10) Patent No.: US 7,613,590 B2
(45) Date of Patent: *Nov. 3, 2009

(54) MODULAR MICROPROCESSOR-BASED POWER TOOL SYSTEM

(75) Inventor: Stephen J. Brown, Woodside, CA (US)

(73) Assignee: Health Hero Network, Inc., Redwood City, CA (US)

( * ) Notice: Subject to any disclaimer, the term of this patent is extended or adjusted under 35 U.S.C. 154(b) by 807 days.

This patent is subject to a terminal disclaimer.

(21) Appl. No.: 11/272,816

(22) Filed: Nov. 15, 2005

(65) Prior Publication Data

US 2006/0155582 A1   Jul. 13, 2006

Related U.S. Application Data

(63) Continuation-in-part of application No. 09/422,046, filed on Oct. 20, 1999, which is a continuation of application No. 09/271,217, filed on Mar. 17, 1999, now Pat. No. 6,168,563, which is a continuation-in-part of application No. 08/946,341, filed on Oct. 7, 1997, now Pat. No. 5,997,476, which is a continuation-in-part of application No. 08/847,009, filed on Apr. 30, 1997, now Pat. No. 5,897,493, and a continuation-in-part of application No. 08/481,925, filed on Jun. 7, 1995, now Pat. No. 5,899,855, which is a continuation of application No. 08/233,397, filed on Apr. 26, 1994, now abandoned, which is a continuation-in-part of application No. 07/977,323, filed on Nov. 17, 1992, now Pat. No. 5,307,263.

(60) Provisional application No. 60/041,746, filed on Mar. 28, 1997, provisional application No. 60/041,751, filed on Mar. 28, 1997.

(51) Int. Cl.
G06F 11/00 (2006.01)

(52) U.S. Cl. ............... 702/188; 702/33; 702/104; 340/500; 340/680; 700/175; 700/180; 82/173

(58) Field of Classification Search ............... 702/1, 702/33, 104, 105, 188; 340/500, 680; 700/175, 700/180; 82/173
See application file for complete search history.

(56) References Cited

U.S. PATENT DOCUMENTS 3,426,150 A    2/1969 Tygart (Continued)

FOREIGN PATENT DOCUMENTS

EP    0286456    10/1988

(Continued)

OTHER PUBLICATIONS

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

(Continued)

*Primary Examiner*—Edward Raymond
*Assistant Examiner*—Elias Desta
(74) *Attorney, Agent, or Firm*—Christopher P. Maiorana, PC

(57) ABSTRACT

A power tool system and method of using the same is provided. The system can include a programmable microprocessor device including at least one input mechanism, and a memory having instructions and/or other information. The system can also include a display; at least one power tool having at least one sensor operable for monitoring a parameter associated with operation of the power tool. The system can further include a communications device connectable in signal communication with both the programmable microprocessor device and the at least one sensor and program instructions. The method can include the steps of (i) using stored program instructions to generate power tool related information on at least one display and (ii) collecting power tool related data using a programmable microprocessor.

43 Claims, 15 Drawing Sheets

U.S. PATENT DOCUMENTS

| | | |
|---|---|---|
| 3,566,365 A | 2/1971 | Rawson et al. |
| 3,566,370 A | 2/1971 | Worthington, Jr. et al. |
| 3,581,072 A | 5/1971 | Nymeyer |
| 3,768,014 A | 10/1973 | Smith |
| 3,811,116 A | 5/1974 | Takeuchi, et al. |
| 3,883,235 A | 5/1975 | Lynn, et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. |
| 4,546,436 A | 10/1985 | Schneider et al. |
| 4,549,179 A * | 10/1985 | Stendardo .............. 340/825.69 |
| 4,566,461 A | 1/1986 | Lubell et al. |
| 4,576,578 A | 3/1986 | Parker et al. |
| 4,592,258 A * | 6/1986 | Halm ........................ 81/57.4 |
| 4,592,546 A | 6/1986 | Fascenda et al. |
| 4,627,445 A | 12/1986 | Garcia et al. |
| 4,636,137 A * | 1/1987 | Lemelson ................... 414/730 |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |

| | | | | | | |
|---|---|---|---|---|---|---|
| 5,304,112 A | 4/1994 | Mrklas et al. | | 5,597,307 A | 1/1997 | Redford et al. |
| 5,304,468 A | 4/1994 | Phillips et al. | | 5,601,435 A | 2/1997 | Quy |
| 5,307,263 A | 4/1994 | Brown | | 5,613,495 A | 3/1997 | Mills et al. |
| 5,309,919 A | 5/1994 | Snell et al. | | 5,619,991 A | 4/1997 | Sloane |
| 5,321,009 A | 6/1994 | Baeder et al. | | 5,624,265 A | 4/1997 | Redford et al. |
| 5,325,288 A | 6/1994 | Satou | | 5,628,309 A | 5/1997 | Brown |
| 5,329,459 A | 7/1994 | Kaufman et al. | | 5,629,981 A | 5/1997 | Nerlikar |
| 5,329,608 A | 7/1994 | Bocchieri et al. | | 5,631,844 A | 5/1997 | Margrey et al. |
| 5,331,549 A | 7/1994 | Crawford, Jr. | | 5,633,910 A | 5/1997 | Cohen |
| 5,333,981 A | 8/1994 | Pronovost et al. | | 5,635,532 A | 6/1997 | Samid |
| 5,335,338 A | 8/1994 | Proesel | | 5,640,569 A | 6/1997 | Miller et al. |
| 5,339,821 A | 8/1994 | Fujimoto | | 5,640,953 A | 6/1997 | Bishop et al. |
| 5,341,291 A | 8/1994 | Roizen et al. | | 5,642,731 A | 7/1997 | Kehr |
| 5,343,239 A | 8/1994 | Lappington et al. | | 5,642,936 A | 7/1997 | Evans |
| 5,344,324 A | 9/1994 | O'Donnell et al. | | 5,651,363 A | 7/1997 | Kaufman et al. |
| 5,357,427 A | 10/1994 | Langen et al. | | 5,651,775 A | 7/1997 | Walker et al. |
| 5,366,896 A | 11/1994 | Margrey et al. | | 5,659,691 A | 8/1997 | Durward et al. |
| 5,368,562 A | 11/1994 | Blomquist et al. | | 5,666,487 A | 9/1997 | Goodman et al. |
| 5,371,687 A | 12/1994 | Holmes, II et al. | | 5,670,711 A | 9/1997 | Detournay et al. |
| 5,375,604 A | 12/1994 | Kelly et al. | | 5,675,635 A | 10/1997 | Vos et al. |
| 5,377,100 A | 12/1994 | Pope et al. | | 5,678,562 A | 10/1997 | Sellers |
| 5,390,238 A | 2/1995 | Kirk et al. | | 5,678,571 A | 10/1997 | Brown |
| 5,399,821 A | 3/1995 | Inagaki et al. | | 5,679,075 A | 10/1997 | Forrest et al. |
| 5,410,471 A | 4/1995 | Alyfuku et al. | | 5,680,590 A | 10/1997 | Parti |
| 5,410,474 A | 4/1995 | Fox | | 5,680,866 A | 10/1997 | Kangas et al. |
| 5,429,140 A | 7/1995 | Burdea et al. | | 5,687,322 A | 11/1997 | Deaton et al. |
| 5,431,690 A | 7/1995 | Schaldach et al. | | 5,687,717 A | 11/1997 | Halpern et al. |
| 5,431,691 A | 7/1995 | Snell et al. | | 5,687,734 A | 11/1997 | Dempsey et al. |
| 5,434,611 A | 7/1995 | Tamura | | 5,689,652 A | 11/1997 | Lupien et al. |
| 5,438,607 A | 8/1995 | Przygoda, Jr. et al. | | 5,692,906 A | 12/1997 | Corder |
| 5,438,983 A | 8/1995 | Falcon | | 5,704,364 A | 1/1998 | Saltzstein et al. |
| 5,441,047 A | 8/1995 | David et al. | | 5,704,366 A | 1/1998 | Tacklind et al. |
| 5,449,334 A | 9/1995 | Kingsbury | | 5,704,902 A | 1/1998 | Vandenbelt et al. |
| 5,454,721 A | 10/1995 | Kuch | | 5,704,922 A | 1/1998 | Brown |
| 5,454,722 A | 10/1995 | Holland et al. | | 5,710,178 A | 1/1998 | Samid |
| 5,456,606 A | 10/1995 | McIntyre | | 5,710,918 A | 1/1998 | Lagarde et al. |
| 5,456,692 A | 10/1995 | Smith, Jr. et al. | | 5,711,297 A | 1/1998 | Iliff |
| 5,458,123 A | 10/1995 | Unger | | 5,714,319 A | 2/1998 | Joutel et al. |
| 5,467,269 A | 11/1995 | Flaten | | 5,715,451 A | 2/1998 | Marlin |
| 5,471,039 A | 11/1995 | Irwin, Jr. et al. | | 5,715,823 A | 2/1998 | Wood et al. |
| 5,471,382 A | 11/1995 | Tallman et al. | | 5,717,739 A | 2/1998 | Dyer et al. |
| 5,483,276 A | 1/1996 | Brooks et al. | | 5,717,913 A | 2/1998 | Driscoll |
| 5,488,412 A | 1/1996 | Majeti et al. | | 5,720,733 A | 2/1998 | Brown |
| 5,488,423 A | 1/1996 | Walkingshaw et al. | | 5,722,418 A | 3/1998 | Bro |
| 5,501,231 A | 3/1996 | Kaish | | 5,727,153 A | 3/1998 | Powell |
| 5,502,636 A | 3/1996 | Clarke | | 5,730,124 A | 3/1998 | Yamauchi |
| 5,502,726 A | 3/1996 | Fischer | | 5,730,654 A | 3/1998 | Brown |
| 5,504,519 A | 4/1996 | Remillard | | 5,732,696 A | 3/1998 | Rapoport et al. |
| 5,517,405 A | 5/1996 | McAndrew et al. | | 5,732,709 A | 3/1998 | Tacklind et al. |
| 5,518,001 A | 5/1996 | Snell | | 5,734,413 A | 3/1998 | Lappington et al. |
| 5,519,058 A | 5/1996 | Gonick et al. | | 5,749,083 A | 5/1998 | Koda et al. |
| 5,519,433 A | 5/1996 | Lappington et al. | | 5,752,234 A | 5/1998 | Withers |
| 5,523,232 A | 6/1996 | Sechler | | 5,754,740 A | 5/1998 | Fukuoka et al. |
| 5,536,249 A | 7/1996 | Castellano et al. | | 5,760,771 A | 6/1998 | Blonder et al. |
| 5,542,420 A | 8/1996 | Goldman et al. | | 5,772,585 A | 6/1998 | Lavin et al. |
| 5,544,649 A | 8/1996 | David et al. | | 5,778,882 A | 7/1998 | Raymond et al. |
| 5,546,943 A | 8/1996 | Gould | | 5,782,814 A | 7/1998 | Brown et al. |
| 5,549,117 A | 8/1996 | Tacklind et al. | | 5,785,650 A | 7/1998 | Akasaka et al. |
| 5,550,575 A | 8/1996 | West et al. | | 5,787,295 A | 7/1998 | Nakao |
| 5,553,609 A | 9/1996 | Chen et al. | | 5,788,428 A * | 8/1998 | Ward et al. .................. 408/1 R |
| 5,558,638 A | 9/1996 | Evers et al. | | 5,791,342 A | 8/1998 | Woodard |
| 5,564,429 A | 10/1996 | Bornn et al. | | 5,792,117 A | 8/1998 | Brown |
| 5,569,212 A | 10/1996 | Brown | | 5,793,969 A | 8/1998 | Kamentsky et al. |
| 5,572,421 A | 11/1996 | Altman et al. | | 5,794,219 A | 8/1998 | Brown |
| 5,572,646 A | 11/1996 | Kawai et al. | | 5,794,251 A | 8/1998 | Watanabe et al. |
| 5,574,828 A | 11/1996 | Hayward et al. | | 5,796,393 A | 8/1998 | MacNaughton et al. |
| 5,576,952 A | 11/1996 | Stutman et al. | | 5,799,318 A | 8/1998 | Cardinal et al. |
| 5,583,758 A | 12/1996 | McIlroy et al. | | 5,800,458 A | 9/1998 | Wingrove |
| 5,590,648 A | 1/1997 | Mitchell et al. | | 5,802,494 A | 9/1998 | Kuno |
| 5,593,349 A | 1/1997 | Miguel et al. | | 5,802,534 A | 9/1998 | Hatayama et al. |
| 5,593,390 A | 1/1997 | Castellano et al. | | 5,806,057 A | 9/1998 | Gormley et al. |
| 5,594,637 A | 1/1997 | Eisenberg et al. | | 5,810,747 A | 9/1998 | Brudny et al. |
| 5,596,994 A | 1/1997 | Bro | | 5,819,735 A | 10/1998 | Mansfield et al. |

| | | | | | | |
|---|---|---|---|---|---|---|
| 5,822,544 | A | 10/1998 | Chaco et al. | 6,210,272 B1 | 4/2001 | Brown |
| 5,822,715 | A | 10/1998 | Worthington et al. | 6,221,012 B1 | 4/2001 | Maschke et al. |
| 5,825,283 | A | 10/1998 | Camhi | 6,233,539 B1 | 5/2001 | Brown |
| 5,827,180 | A | 10/1998 | Goodman | 6,240,393 B1 | 5/2001 | Brown |
| 5,828,943 | A | 10/1998 | Brown | 6,248,065 B1 | 6/2001 | Brown |
| 5,832,448 | A | 11/1998 | Brown | 6,260,022 B1 | 7/2001 | Brown |
| 5,835,896 | A | 11/1998 | Fisher et al. | 6,270,455 B1 | 8/2001 | Brown |
| 5,840,020 | A | 11/1998 | Heinonen et al. | 6,270,456 B1 | 8/2001 | Iliff |
| 5,842,976 | A | 12/1998 | Williamson | 6,334,778 B1 | 1/2002 | Brown |
| 5,868,669 | A | 2/1999 | Iliff | 6,352,523 B1 | 3/2002 | Brown et al. |
| 5,868,683 | A | 2/1999 | Protopapas et al. | 6,368,273 B1 | 4/2002 | Brown |
| 5,875,432 | A | 2/1999 | Sehr | 6,370,513 B1 | 4/2002 | Kolawa et al. |
| 5,879,163 | A | 3/1999 | Brown et al. | 6,375,469 B1 | 4/2002 | Brown |
| 5,882,338 | A | 3/1999 | Gray | 6,379,301 B1 | 4/2002 | Worthington et al. |
| 5,887,133 | A | 3/1999 | Brown et al. | 6,381,577 B1 | 4/2002 | Brown |
| 5,893,077 | A | 4/1999 | Griffin | 6,436,036 B1 | 8/2002 | Miller-Kovach et al. |
| 5,893,098 | A | 4/1999 | Peters et al. | 6,513,532 B2 | 2/2003 | Mault et al. |
| 5,897,493 | A | 4/1999 | Brown | 2002/0019748 A1 | 2/2002 | Brown |
| 5,899,855 | A | 5/1999 | Brown | 2004/0106855 A1 | 6/2004 | Brown |
| 5,911,687 | A | 6/1999 | Sato et al. | 2004/0107116 A1 | 6/2004 | Brown |
| 5,913,310 | A | 6/1999 | Brown | 2004/0117207 A1 | 6/2004 | Brown |
| 5,918,603 | A | 7/1999 | Brown | 2004/0117208 A1 | 6/2004 | Brown |
| 5,920,477 | A | 7/1999 | Hofbert et al. | 2004/0117209 A1 | 6/2004 | Brown |
| 5,933,136 | A | 8/1999 | Brown | 2004/0117210 A1 | 6/2004 | Brown |
| 5,935,060 | A | 8/1999 | Iliff | | | |
| 5,940,801 | A | 8/1999 | Brown | | | |
| 5,941,829 | A | 8/1999 | Saltzstein et al. | | | |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| JP | 1995407095963 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

| | | | |
|---|---|---|---|
| 5,945,651 | A | 8/1999 | Chorosinski et al. |
| 5,951,300 | A | 9/1999 | Brown |
| 5,954,641 | A | 9/1999 | Kehr et al. |
| 5,956,501 | A | 9/1999 | Brown |
| 5,960,403 | A | 9/1999 | Brown |
| 5,961,446 | A | 10/1999 | Beller et al. |
| 5,966,526 | A | 10/1999 | Yokoi |
| 5,971,855 | A | 10/1999 | Ng |
| 5,971,922 | A | 10/1999 | Arita et al. |
| 5,983,003 | A | 11/1999 | Lection et al. |
| 5,983,217 | A | 11/1999 | Khosravi-Sichani et al. |
| 5,987,471 | A | 11/1999 | Bodine et al. |
| 5,995,969 | A | 11/1999 | Lee et al. |
| 5,997,476 | A | 12/1999 | Brown |
| 5,997,502 | A | 12/1999 | Reilly et al. |
| 6,001,065 | A | 12/1999 | DeVito |
| 6,022,315 | A | 2/2000 | Iliff |
| 6,022,615 | A | 2/2000 | Rettenbacher |
| 6,023,686 | A | 2/2000 | Brown |
| 6,024,281 | A | 2/2000 | Shepley |
| 6,029,138 | A | 2/2000 | Khorasani et al. |
| 6,032,119 | A | 2/2000 | Brown et al. |
| 6,035,328 | A | 3/2000 | Soukal |
| 6,046,761 | A | 4/2000 | Echerer |
| 6,049,794 | A | 4/2000 | Jacobs et al. |
| 6,050,940 | A | 4/2000 | Braun et al. |
| 6,055,314 | A | 4/2000 | Spies et al. |
| 6,055,487 | A | 4/2000 | Margery et al. |
| 6,055,506 | A | 4/2000 | Frasca, Jr. |
| 6,057,758 | A | 5/2000 | Dempsey et al. |
| 6,068,615 | A | 5/2000 | Brown et al. |
| 6,095,985 | A | 8/2000 | Raymond et al. |
| 6,101,478 | A | 8/2000 | Brown |
| 6,110,148 | A | 8/2000 | Brown et al. |
| 6,113,578 | A | 9/2000 | Brown |
| 6,138,145 | A | 10/2000 | Kawanaka |
| 6,144,837 | A | 11/2000 | Quy |
| 6,151,586 | A | 11/2000 | Brown |
| 6,161,095 | A | 12/2000 | Brown |
| 6,167,362 | A | 12/2000 | Brown et al. |
| 6,167,386 | A | 12/2000 | Brown |
| 6,168,563 | B1 | 1/2001 | Brown |
| 6,177,940 | B1 | 1/2001 | Bond et al. |
| 6,186,145 | B1 | 2/2001 | Brown |
| 6,189,029 | B1 | 2/2001 | Fuerst |
| D439,242 | S | 3/2001 | Brown et al. |

OTHER PUBLICATIONS

Jaffrey et al.; "PIN: An Associated Protein Inhibitor of Neuronal Nitric Oxide Synthase"; Science; vol. 274; Nov. 1, 1996; Ref: XP 002050141.

"Blood Glucose Monitors", Portable Health Device, (1998), vol. 17(9), pp. 253-271.

"Talking Nano Puppy"; retrieved from URL http://www.virtualpet.com/vp/farm/nano/talkn/talkn.htm Apr. 23, 2000.

Voelker, Rebecca, "Shoe Leather Therapy is Gaining on TB", Jama, (Mar. 13, 1996), vol. 275, 743.

"Digital Doggie"; retrieved from URL http://www.virtualpet.com/vp/farm/gigapet/ddoggie.htm Apr. 23, 2000.

Anonymous, "Health Hero Network, Inc. Receives First-Ever FDA Clearance for Connecting Medical Devices to Internet", PR Newswire, (Dec. 2, 1993), 3 pages.

"Playmates Toys deals knockout blow to virtual pet competitors with introduction of Nano Fighter™ For Boys"; New Nano Pet Fighting Pet Press Release; retrieved from URL http://www.virtualpet.com/vp/farm/nano/nfightpr.htm Apr. 23, 2000.

Updike, Stuart J., et al., "Laboratory Evaluation of New Reusable Blood Glucose Sensor", Diabetes Care, (Nov./Dec. 1998), vol. 11, No. 10, pp. 801-807.

RO_Auction Auctioneers Property Database System and RO_Auction Auctioneers Accounting System; RO-Auction features; Dec. 4, 1995.

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Reis, H, "Telemedicine: Transmitting Expertise to the Point of Care Toward an Electronic Patient Record"; '97, Nashville, TN, Apr. 27-May 3, 1997, pp. 248-256, v. 3.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

United Healthcare's OPTUM Division goes online to better health by announcing a unique internet application. PR Newswire, p0801MNTH004. Aug. 1, 1996.

Hunter, "Technological Advances in Bedside Monitoring: Biosensors", Archives and Laboratory Medicine, (Jul. 1987), pp. 633-636.

Telemedicine Provides Two-Way Computer Link for Parents of Very Premature Infants. PR Newswire. p1007NEM034. Oct. 7, 1996.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Save the earth artrock auction, http://www.commerce.com.save-earth. Auction Web, http://www.ebay.com.

Makikawa, M., et al., "Microprocessor-Based Memory Device for Ambulatory Heart Rate and and Physical Activity Recording", Methods of Information in Medicine, (1994), vol. 33, No. 1, pp. 94-96.

Luebke, Cathy, "Barrett-Jackson Auction Turns High-Tech", Business Journal, vol. 16, Issue 12, pp. 11, Jan. 19, 1996.

Schenkels, P., "Supplementary European Search Report", Application No. EP 97 92 2716, (Mar. 11, 2002).

"Theme Hospital," product review 1996 [retrieved Apr. 21, 2000], Retrieved from <URL:www.vigilante.co.uk/ep/misc/hospital.htm>.

Potter, David, "Fundamentals of PC-Based Data Acquisition", Sensors, (Feb. 1994), pp. 12-20.

"Virtual Tomagutchi," 1998 [retrieved Apr. 23, 2000], Retrieved from <URL:www.sttf.org/english/action/tomagutchi.html>.

Roberts; "Diabetes and Stress: A Type A Connection?", Psychology Today, (Jul. 1987), v. 21; pp. 22(1); Dialog: File 149, Acc# 05038381.

"Virtual Pet Product Reviews," 1997 [retrieved on Apr. 23, 2000], Retrieved from <URL:www.virtualpet.com/vp/farm/reviews/reviews,htm>.

Soeldner, J. S., "Treatment of Diabetes mellitus by Devices", The American Journal of Medicine, (Jan. 1981), vol. 70, 183-194.

"Giga Pets," 1997 [retrieved on Apr. 23, 2000], Retrieved from <URL:www.virtualpet.com/vp/farm/gigapet/gigapet.htm>.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.

"Towards a partnership of care", M2 Presswire, Jun. 14, 2000.

Moore, "New Applications Break Through Storage Boundaries", Computer Technology Review, (Oct. 1999), vol. 19, No. 10 p. 1.

"Who Will Dominate The Desktop in the 90's?", Jack Shandle, Electronics, Feb. 1990, pp. 48-50. (3 pages) Cited by 2 patents.

Howey, et al., "A Rapidly Absorbed Analogue of Human Insulin"; Diabetes, vol. 43, Mar. 1994, pp. 396-402. (7 pages).

Jimison et al., "Patient-Specific explanation in models of chronic disease", Revised Feb. 1992 Artificial Intelligence in Medicine 4 (1992) 191-205.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

Jones, Chris, "Microsoft readies DocObject; technology will allow document editing in Web browsers", InfoWorld, v18 n18 p. 48(1), Apr. 29, 1996.

"AdOptimizer—Ad Management Software for Websites", Newsbytes, pNEW10040041, Oct. 4, 1996.

"New Horizons teams with Duke, Real Media"; The Seybold Report on Desktop Publishing, v10 n12 p. 24(1), Aug. 12, 1996.

Marsh, David G. "Approaches Toward the Genetic Analysis of Complex Traits Asthma and Atrophy", Am. J. Respir.Crit.Care Med., (1997), vol. 156, pp. S-133-S138.

Mims; "Psychological Testing"; Computers & Electronics; v23; p. 22(6); Feb. 1985; Dialog: File 47, Acc# 2654858.

Wilkins, Aaron. "Expanding Internet access for health care consumers", Health Care Management Review, Summer, Jul. 1999, 24-30.

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Leyerle, Beverly J., et al., "The PDMS as a Focal Point for Distributed Patient Data", International Journal of Clinical Monitoring and Computing, (1988), vol. 5, pp. 155-161.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Octogotchi Instruction Manual, 1997. Dino-Kun Instruction Manual, 1997.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Latman, N.S., "Evaluation of Electronic, Digital Blood Glucose Monitors", Biomedical Instrumentation and Technology, (1991), vol. 25, No. 1, 43-49.

Edelson; "Fashion Reevaluates Flickering Fortunes of TV Home Shopping"; WWD; v170 n87; p. 1(3); Nov. 8, 1995; Dialog: File 148, Acc#08289119.

Results of the world's first on-line auction, http://www.christies.com.

"Cathay Pacific Airways-USA to Hold First-Ever Internet CyberAuction; CyberTravelers Can Bid for 50 Business Class Round Trips to Hong Kong—No Minimum Bid"; Business Wire; p. 9261084; Sep. 26, 1995; Dialog: File 148, Acc#08167091.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

"Onsale Onsale Brings Thrill of Auctions and Bargain Hunting Online: Unique Internet retail service debuts with week-long charity auction for The Computer Museum in Boston", May 24, 1995; Dialog Abstract: File 610, Acc#0489267.

"Playmates Toys leads Americas virtual pet craze into its next generation by introducting talking Nano Pals"; Talking Nano Pet Press Release; Nov. 18, 1997; retrieved from URL http://www.virtualpet.com/vp/farm/nano/talkn/tnpress.htm on Apr. 23, 2000.

O'Donnell; "Alan's At It Again"; Bond Buyer; v309 n29448; p. 1(3); Jul. 21, 1994; Dialog: File 148, Acc#07478152.

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Gauntlet (for PC) rulebook by Mindscape Inc. (Gauntlet by Apple);1985.

Brenman Et Al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

Bai, "Design of home healthcare network", IEEE 1997 pp. 1657-1658.

Horio, Hiroyuki, et al., "Clinical Telecommunication Network System for Home Monitoring", Medical & Biological Engineering & Computing, (Mar. 1994), vol. 32, 227-230.

"The description of the Tandy Radio Shack TRS-80 Model 100/102 device available at http://www.old-computuers.com/musuem/computer.asp?c=233", World Wide Web, (Feb. 13, 2004), 1-3.

Brunetti, P., et al., "A Simulation Study on a Self-Turning Portable Controller of Blood Glucose", The International Journal of Artificial Organs, (1993), vol. 16, No. 16, pp. 51-57.

Cheng, Joe H., "PCT Search Report", (Jan. 11, 1996).

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator?", The Medical Journal of Australia, (Oct. 5, 1992), vol. 157, 489-491.

Lacyk, John, "PCT Search Report", (Jun. 12, 1997).

Miles, Laughton E., "A Portable Microcomputer for Long-Term Physiological Monitoring in the Home and Work Environment", Medical Monitoring in the Home and Work Environment, (1990), pp. 47-57.

Giuffrida, et al., Should We Pay the Patient? Review of Financial Incentives to enhance Patient Compliance:, Biomedical Journal, (1997), vol. 315, pp. 703-707.

Pfeiffer, E. F., "The Glucose Sensor: The Missing Link in Diabetes Therapy", Hormone and Metabolic Research, (1990), vol. 24m Suppl. pp. 154-164.

Schork, Nicholas J., "Genetics of Complex Disease", Am.J.Respir. Crit. Care Me., (1997), vol. 156, pp. S103-S109.

Shandle, Jack, "Who will dominate the desktop in the 90's?", Electronics, (Feb. 1990), pp. 48-50.

Finston, "Parent+Teacher=Healthy Child", Diabetes Forecast, (Apr. 1994), v47 n9; p. 26(5); Dialog: file 149, Acc# 15804228.

M.U.L.E. rulebook by Electronic Arts, 1983.

"Onsale Joins Fray as Online Shopping Picks Up Speed: Internet Booms"; Computer Reseller News; Jun. 5, 1995; p. 73; Dialog: File 16, Acc#05649796.

Siegmann;"Nowhere to Go but Up"; PC Week; v12 n42, p. A5(1); Oct. 23, 1995; Dialog: File 148, Acc#08222496.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Adilman; "Videogames: Knowing the Score"; Creative Computing; v9; p. 224(5); Dec. 1983; Dialog: File 148, Acc# 01891055.

Marx, Wendy, "More than just the Scores: ESPNET SportsZone is a model for expanding brand names online", InformationWeek, n576 p. 61(2), Apr. 22, 1996.

Skolnick et al. "Simultaneous Analysis of Multiple Polymorphic Loci Using Amplified Sequence Polymorphisms (ASPs)"; Genomics. 2: 273-279.

Caprihan, A., et al., "A Simple Microcomputer for Biomedical Signal Processing", IECI '78 Annual Conference Proceedings on Industrial Applications of Microprocessors, (Mar. 20, 1978), 18-23.

"Tamagotchi," 1997 [retrieved on Apr. 23, 2000], Retrieved from <URL:www.virtualpet.com/vp/farm/lleg/lleg.htm>.

"Putting the Lot on the Net", Antique Collector, vol. 66, Issue 9, p. 26, Downloaded from Corporate Resource Net, Nov./Dec. 1995.

Lachnit, Carroll, "Hawkin's Online Auction", Photo District News, vol. 16, Issue 1, p. 18, Jan. 1996.

Bruce, "Health Hero Network CEO, CNNfn", Digital Jam, (Dec. 1, 1999), 3.

"Cathay Pacific Airways-USA receives more than 1,300 bids during first five days of CyberAuction"; Business Wire, Oct. 18, 1995, p. 10181119.

"Nano Fighter Pets"; retrieved from URL http://www.virtualpet.com/vp/farm/nano/nfighter.htm Apr. 23, 2000.

"Giga Farm"; retrieved from URL http://www.virtualpet.com/vp/farm/gigapet/gpfarm/gpfarm.htm Apr. 23, 2000.

Billiard, A., et al. "Telematic Transmission of Computerized Blood Glucose Profiles for IDDm Patients", Diabetes Care, (Feb. 1991), vol. 14, No. 2, pp. 130-134.

Bower, "Brain Clues to Energy-efficient Learning", Science News, (Apr. 1992), v. 141; p. 215(1); Dialog: File 647, Acct# 12123949.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Kaufman, Steven, B., "The Learning Game", Nation's Business, (Nov. 1993).

Albisser, A.M. "Intelligent Instrumentation in Diabetic Management", CRC Critical Reviews in Biomedical Engineering, vol. 17, No. 1, pp. 1-24.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Wyatt, J. C., "Clinical Data Systems, Part 2: Components and Techniques", Lancet, (Dec. 1994), vol. 344, No. 8937, pp. 1609-1614.

Gordon; "Auctions Become High Tech"; Dealer Business; v29 n7; p. 21(4); Mar. 1995; Dialog: File 148, Acc#07862519.

"Introducing the Next Generation of About Your Diabetes", U.S. Pharmacopical Convention and American Diabetes Association, (1993).

Hutheesing, Nikhil, "An on-line gamble", Forbes, v157 n10 p. 288(1), May 20, 1996.

"Future of the Virtual Pet Industry," 1997 [retrieved on Apr. 23, 2000], Retrieved from <URL:www.virtualpet.com/vp/future/future.htm>.

DigiPet Instruction Manual, 1997.

"European Search Report", From 6858P005EP, (Mar. 27, 1998).

"Nano Baby Instructions"; retrieved from file://C:\My Documents\Nano Baby Instructions.htm Apr. 23, 2000.

"How Flash Memory Works", Internet printout of URL address: http://www.howstuffworks.com/flash-memory4.htm, (Sep. 28, 2002), 2 pages.

Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.

"CD-ROM Mavericks: Proprietary TV-Based Players", Byte Guide to CD-ROM, pp. 100-105.

Vallera, D. A., et al., "Accuracy of Portable Blood Glucose Monitoring", American Journal of Clinical Pathology, (1991), vol. 95, No. 2, pp. 247-252.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Nano Page, 1997 [retrieved on Apr. 23, 2000], Retrieved from <URL:www.virtualpet.com/vp/farm/nano/nano.htm>.

"+5V Powered Isolated RS-232 Drivers/Receivers" Maxim Integrated Products.

"Central Fetal Monitoring Systems with Optical Disk Storage", New Technology Brief, (Nov./Dec. 1998), vol. 2, No. 6, pp. 249-251.

Meissner, et al., "Building an Integrated Clinical and Research Network", Proceedings of the SPIE, (Oct. 24, 1995), vol. 2618, p. 92-99.

Bruce, et al., "The Effects of Sympathetic Nervous System Activation and Psychological Stress . . . "; Diabetologia; 35(9); 1992; 835-843; Dialog: File 5, Acc#9629427. (9 pages).

Schement, "An Intelligent Controller for Neurophysiological Experiments," Proceeding of the Annual Symposium on Computer Based Medical Systems, Durham, Jun. 14-17, 1992, p. 528, line 1-p. 529, line 21.

Martinez, Fernando D., "Complexities of the Genetics of Asthma", Am.J. Respir. Crit. Care Med., (1997), vol. 156, pp. S117-S122.

Spitzer et al.; "The moderating effect of age on self-care"; Western Journal Of Nursing Research, v18, n2, p. 136(13), Apr. 1996.

Research project launched to improve health of America's communities; new Disney community in Florida is focus of program. Business Wire, p. 10011142. Oct. 1, 1996.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

+5V Powered Isolated RS-232 Drivers/Receivers Maxim Integrated Products.

AdOptimizer—Ad Management Software for Websites, Newsbytes, pNEW10040041, Oct. 4, 1996.

Antique Collector, Putting the Lot on the Net, vol. 66, Issue 9, p. 26, Downloaded from Corporate Resource Net, Nov./Dec. 1995.

Blood Glucose Monitors, Portable Health Device, (1998), vol. 17(9), pp. 253-271.

Cathay Pacific Airways-USA receives more than 1,300 bids during first five days of CyberAuction; Business Wire, Oct. 18, 1995, p. 10181119.

Cathay Pacific Airways-USA to Hold First-Ever Internet CyberAuction; CyberTravelers Can Bid for 50 Business Class Round Trips to Hong Kong—No Minimum Bid; Business Wire; p. 9261084; Sep. 26, 1995; Dialog: File 148, Acc#08167091.

CD-ROM Mavericks: Proprietary TV-Based Players, Byte Guide to CD-ROM, pp. 100-105.

Central Fetal Monitoring Systems with Optical Disk Storage, New Technology Brief, (Nov./Dec. 1998), vol. 2, No. 6, pp. 249-251.

Digital Doggie; retrieved from URL http://www.virtualpet.com/vp/farm/gigapet/ddoggie.htm Apr. 23, 2000.

EP European Search Report, From 6858P005EP, (Mar. 27, 1998).

Future of the Virtual Pet Industry, 1997 [retrieved on Apr. 23, 2000], Retrieved from <URL:www.virtualpet.com/vp/ future/future.htm>.

Giga Farm; retrieved from URL http://www.virtualpet.com/vp/farm/gigapet/gpfarm.htm Apr. 23, 2000.

Giga Pets, 1997 [retrieved on Apr. 23, 2000], Retrieved from <URL:www.virtualpet.com/vp/farm/gigapet/gigapet.htm>.

Guiffrida, et al., Should We Pay the Patient? Review of Financial Incentives to enhance Patient Compliance:, Biomedical Journal, (1997), vol. 315, pp. 703-707.

How Flash Memory Works, Internet printout of URL address: http://www.howstuffworks.com/flash-memory4.htm, (Sep. 28, 2002), 2 pages.

Introducing the Next Generation of About Your Diabetes, U.S. Pharmacopical Convention and American Diabetes Association, (1993).

Mule. rulebook by Electronic Arts, 1983.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apr. 23, 2000.

Octhigotchi Instruction Manual, 1997. Dino-Kun Instruction Manual, 1997.

Onsale Joins Fray as Online Shopping Picks Up Speed: Internet Booms; Computer Reseller News; Jun. 5, 1995; p. 73; Dialog: File 16, Acc#05649796.

Onsale Onsale Brings Thrill of Auctions and Bargain Hunting Online; Unique Internet retail service debuts with week-long charity auction for the Computer Museum in Boston, May 24, 1995; Dialog Abstract: File 610, Acc#0489267.

Playmates Toys deals knockout blow to virtual pet competitors with introduction of Nano Fighter™ For Boys; New Nano Pet Fighting Pet Press Release; retrieved from URL http://www.virtualpet.com/vp/farm/nano/nfightpr.htm Apr. 23, 2000.

Playmates Toys leads Americas virtual pet craze into its next generation by introducting talking Nano Pals; Talking Nano Pet Press Release; Nov. 18, 1997; retrieved from URL http://www.virtualpet.com/vp/farm/nano/talkn/tnpress.htm on Apr. 23, 2000.

Save the earth artrock auction, http://www.commerce.com.save-earth. Auction Web, http://www.ebay.com.

Schenkels, P., "Supplementary European Search Report", Appl. No. EP 97 92 2716, (Mar. 11, 2002).

Schork, Nicholas J., "Genetics of Complex Disease", Am.J.Respir. Crit. Care Me., (1997), vol. 156, pp. S103-S109.

Seigmann;"Nowhere to Go but Up"; PC Week; v12 n42, p. A5(1); Oct. 23, 1995; Dialog: File 148, Acc#08222496.

Seybold—New Horizons teams with Duke, Real Media; The Seybold Report on Desktop Publishing, v10 n12 p. 24(1), Aug. 12, 1996.

Shandle, Jack, "Who Will Dominate The Desktop in the 90's?", , Electronics, Feb. 1990, pp. 48-50. (3 pages) Cited by 2 patents.

Soeldner, J. S., "Treatment of Diabetes Mellitus by Devices", The American Journal of Medicine, (Jan. 1981), vol. 70, 183-194.

Talking Nano Puppy; retrieved from URL http://www.virtualpet.com/vp/farm/nano/talkn/talkn.htm Apr. 23, 2000.

Tamagotchi, 1997 [retrieved on Apr. 23, 2000], Retrieved from <URL:www.virtualpet.com/vp/farm/lleg/lleg.htm>.

Tandy Radio Shack, "The description of the Tandy Radio Shack TRS-80 Model 100/102 device available at http://www.old-computuers.com/musuem/computer.asp?c=233", World Wide Web, (Feb. 13, 2004), 1-3.

Theme Hospital, product review 1996 [retrieved Apr. 21, 2000], Retrieved from <URL:www.vigilante.co.uk/ep/misc/hospital.htm>.

Towards a partnership of care, M2 Presswire, Jun. 14, 2000.

Virtual Pet Product Reviews, 1997 [retrieved on Apr. 23, 2000], Retrieved from <URL:www.virtualpet.com/vp/farm/reviews/reviews,htm>.

Virtual Tomagutchi, 1998 [retrieved Apr. 23, 2000], Retrieved from <URL:www.stff.org/english/action/tomagutchi.html>.

* cited by examiner

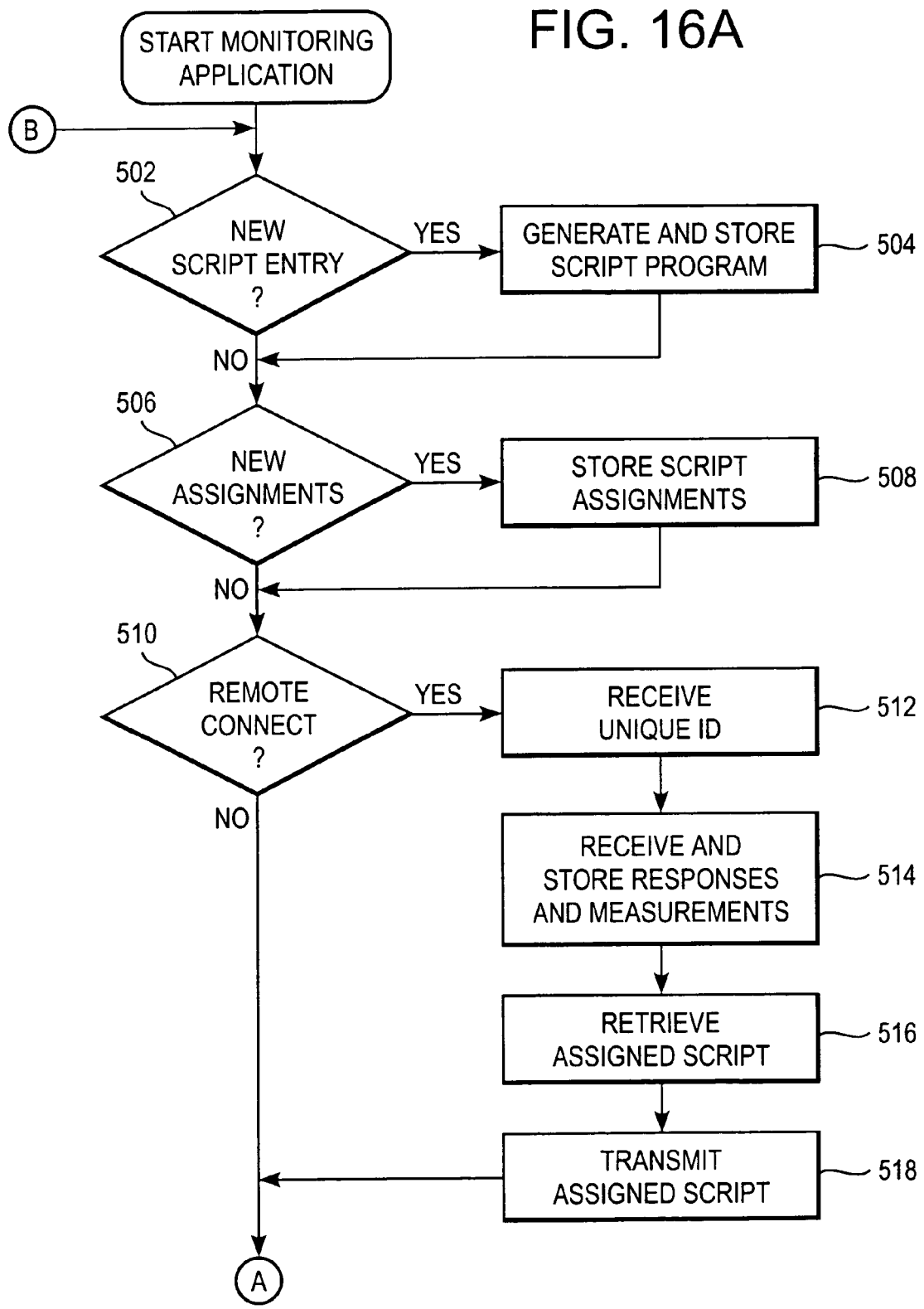

MODULAR MICROPROCESSOR-BASED POWER TOOL SYSTEM

This application is a continuation inpart of application Ser. No. 09/422,046, filed Oct. 20, 1999, which is a continuation of application Ser. No. 09/271,217, filed Mar. 17, 1999, now U.S. Pat. No. 6,168,563, which is (A) a continuation in-part of application Ser. No. 08/946,341, filed Oct. 7, 1997, now U.S. Pat. No. 5,997,476. which is a continuation in-part of application Ser. No. 08/847,009, filed Apr. 30, 1997, now U.S. Pat. No. 5,897,493, which claims the benefit of Provisional application 60/041,746, filed Mar. 28, 1997 and provisional application 60/041,751, filed Mar. 28, 1997 and (B) a continuation in-part of application Ser. No. 08/481,925, filed Jun. 7, 1995, now U.S. Pat. No. 5,899,855, which is a continuation of application Ser. No. 08/233,397, filed Apr. 26, 1994, now abandoned, which is a continuation in-part of application Ser. No. 07/977,323, filed Nov. 17, 1992, now U.S. Pat. No. 5,307,263.

The present application is related to U.S. Pat. Nos. 6,168,563; 6,101,478; 5,897,493; 5,307,263; 5,899,855; 6,381,577; 6,248,065; and 6,368,273, which are hereby incorporated by reference in their entirety.

BACKGROUND

1. Field of the Invention

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The invention is generally directed to power tools and in particular to a microprocessor-based power tool system in which the power tools may be connected to a computer network.

2. Description of the Related Art

Power tools are used in industrial, commercial and consumer venues. Although some of these tools are operated by highly skilled craftsman, many of these tools are not. In fact, there appears to a growing trend toward lesser skilled individuals operating power tools. The decrease in average skill level is apparent both in the industrial shop floor and in the home as more "do-it-yourselfers" choose to undertake major home projects rather than hire professionals. These individuals often to not have the skills to optimally use their power tools, typically resulting in significant waste of time and raw materials. Further, even skilled craftsman may have difficulty detecting minor problems with these tools. For some applications power tools having integrated sensors have been developed to sense certain properties. These power tools can be connected to a computer that monitors limited properties such as tool vibration electrical current, torque, displacement and capacitance. These tools have been used, for example, to improve the quality of fastened items by measuring the torque applied by a nutdriver and preventing the operator from over-torquing the nut. Although these tools can provide some feedback as to their operation, they have not been networked or connected in any way to a remotely located expert, professional, or individual capable of providing help to a power tool user.

Currently, there is a need for a power tool system that allows the operator to send sensed data to a remote service provider, e.g., an expert, or a trained professional using a software based expert system, while operating the power tool. Further, there is a need for a power tool system that allows a remote expert or professional to analyze the sensed data and send messages and/or instructions back to the operator. More significantly, there is a need for a power tool system that allows a remote expert or technician or anyone trained to do the job, to provide instruction to the power tool user in real time or near real time. It would be advantageous to have a power tool system in which sensed data associated with the tool could be sent to a remotely located expert (or technician or anyone trained to do the job), the data evaluated, and instructions sent from the expert to the operator. Further, it would be advantageous to have a system that could do this in real time or near real time to aid the power tool operator in a timely fashion.

SUMMARY OF THE INVENTION

One embodiment of the present invention provides a power tool system comprising a programmable microprocessor device including at least one input mechanism, and a memory having instructions and/or other information; a display; at least one power tool having at least one sensor operable for monitoring a parameter associated with operation of the power tool and for producing digitally encoded signals representative of the monitored parameter; a communications device connectable in signal communication with both the programmable microprocessor device and the at least one sensor; and program instructions for the programmable microprocessor device that, (i) cause instructions and/or other information stored in the memory to be presented to the user on the display, (ii) collect data from a user interaction with the at least one input mechanism in response to the display and stores data in memory, (iii) collect data from the at least one sensor and stores the data in memory, (iv) transmit test results and other data to a remotely located server over a communication network, (v) receive from the server instructions and/or other information stored on the server for transmission to the programmable microprocessor device, and (vi) store instructions and/or other information in the memory.

The present invention also provides a method of using a modular microprocessor power tool system comprising: (a) at a site employing a power tool, (i) using stored program instructions to generate power tool related information on at least one display; (ii) collecting power tool related data using a programmable microprocessor device; (b) connecting at least one remotely located computing facility including at least one central server for communication with a communications device at the power tool site; and (c) providing power tool data to at least one service provider computer remotely located from and in signal communication with the central server, wherein hardware and software of the central server are configured to receive and store power tool-related data from a power tool site that can be viewed or retrieved by an authorized user from the remotely located service provider computer.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 16A is a flow chart illustrating the steps of a method of one embodiment of the invention.

DETAILED DESCRIPTION OF THE EMBODIMENTS

Figure 1:
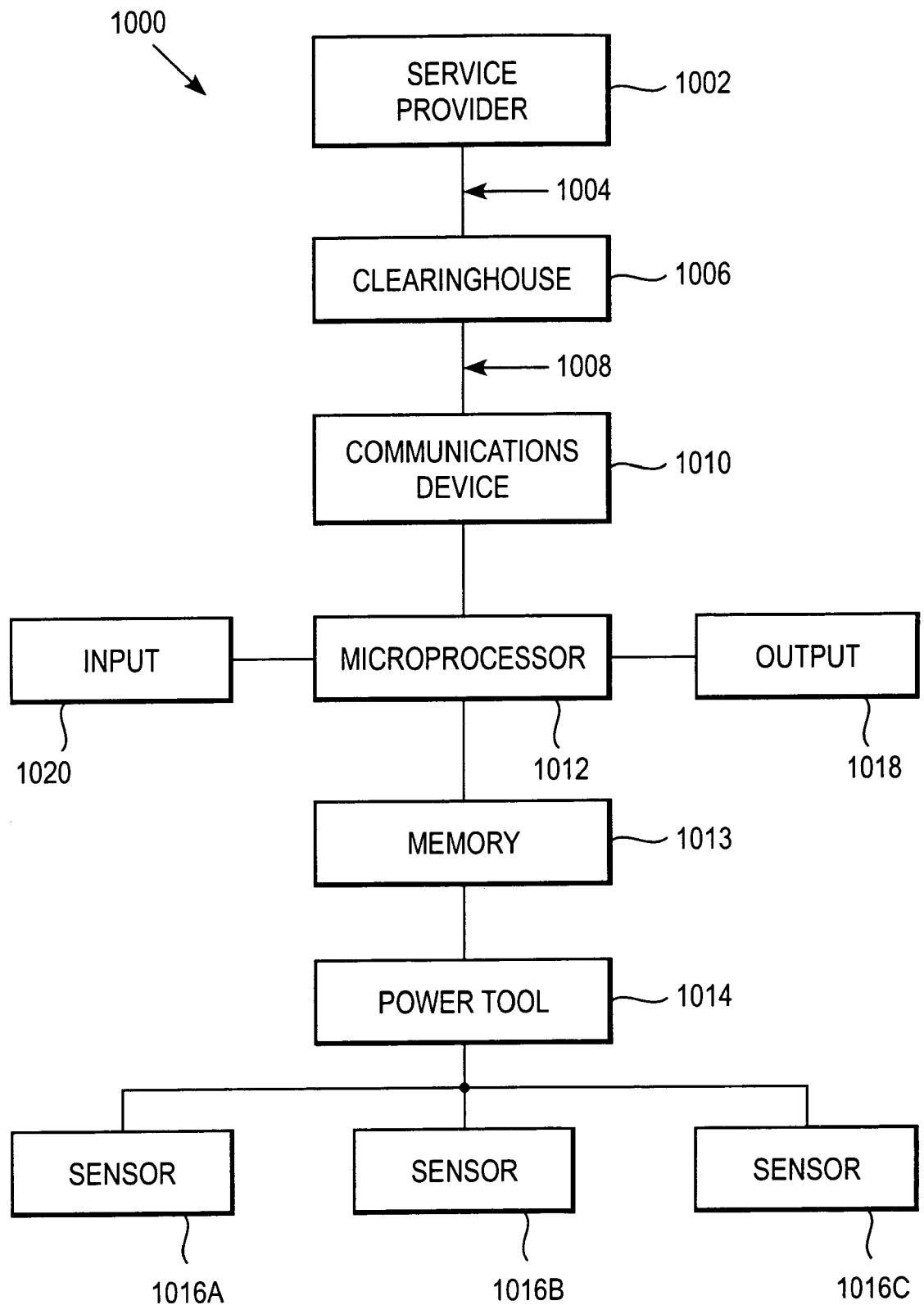
FIG. 1 is a schematic diagram of a power tool system according to one embodiment of the invention.

The present invention, in one embodiment, provides a modular power tool monitoring and management system. Other embodiments of the invention include methods of using power tools employing a modular power tool monitoring and management system. The system may employ a compact microprocessor-based device that includes switches for controlling operation of the unit. The microprocessor-based device processes data supplied by sensors that can be integrated with the power tool to supply signals for displaying relevant information on a display that may be included in the microprocessor-based device or may be integrated into the power tool. The sensors can collect data from the tool and the user's environment and send data to a clearinghouse or central server.

In one embodiment of the invention, data can be sent from a data management device to a remote clearinghouse having a server and from the server to a remotely located service provider. In this embodiment, the system provides for transmission of signals to the remote clearinghouse including, for example, via telephone lines or other transmission media. Preferably, the clearinghouse includes signal processing capability for transmission of reports to the remotely located service provider and for transmission of program instructions to the data management device for adaptation of the power tool. Further, preferably the service provider is a professional in customer service for the tool manufacturer, a retailer, and/or third party program developer of project plans and designs.

In one embodiment of the invention, the system includes a program cartridge operatively connected to the microprocessor-based unit. The program cartridge adapts the microprocessor-based device for operation with various power tools such as a radial arm saw, table saw, jigsaw, router or drill. In one aspect of the invention, a preprogrammed cartridge may be purchased, for example, at retail stores such as hardware stores, home improvement stores, department stores, and the like. In another aspect of the invention, a preprogrammed cartridge can be ordered for delivery through the mail. These cartridges may be ordered, for example, from the tool manufacturer, third party developers/designers, or third party customer service centers. In still another aspect of the invention, the adaptation can occur by downloading program instructions from the clearinghouse server to the cartridge. The program instructions may be selected by the user of the power tool via a website or by the service providers. In other embodiments of the invention, program instructions sent from the clearinghouse reconfigure software in the program cartridge, altering the operation of the power tool. In still another embodiment of the invention, the program cartridge is operatively connected to the power tool via a receptacle in the power tool. In this embodiment, the program cartridge adapts the power tool to supply signals for displaying relevant information on a display that may be included in the microprocessor-based device or may be integrated into the power tool.

In other embodiments, the functionality of the cartridge is incorporated directly into the microprocessor-based device. In still other embodiments, the functionality of the cartridge is incorporated in a memory integrated in the power tool. In all of the above-embodiments, program instructions may be downloaded from the clearinghouse server to adapt or reconfigure the microprocessor or the power tool.

FIG. 1 illustrates a modular microprocessor-base tool system 1000 according to one embodiment of the invention. In this embodiment, a service provider 1002 is in signal connection with a clearinghouse 1006 via a network 1004. The service provider 1002 may be an expert with the use of a given power tool 1014 or a trained technician with access to software instructions on proper use of the power tool 1014. In other embodiments, the service provider may be a professional in customer service for the tool manufacturer, a retailer, and/or third party program developer of project plans and designs.

In this embodiment, the clearinghouse 1006 includes a central server (not shown) that includes memory for storing instructions and messages from the service provider 1002 as well as data and questions/messages from the operator of the power tool 1014. In other embodiments of the invention, the central server includes its software that allows it to analyze data from the power tool 1014. Thus, in these embodiments, the clearinghouse is capable of transferring both "raw" data, that is unprocessed data from the power tool 1014, as well as analyzed data. The analysis software may include statistical analysis tools as well as tools to graphically represent the data.

The clearinghouse is connected to the power tool 1014 via a network 1008. The first and second networks 1004, 1008 have been illustrated as different networks to aid in describing the flow of information between the service provider 1002 and the power tools 1014. However, some or all parts of the networks 1004, 1008 may be the same. That is, data and information may flow over the Internet as part of networks 1004,1008.

Figure 3:
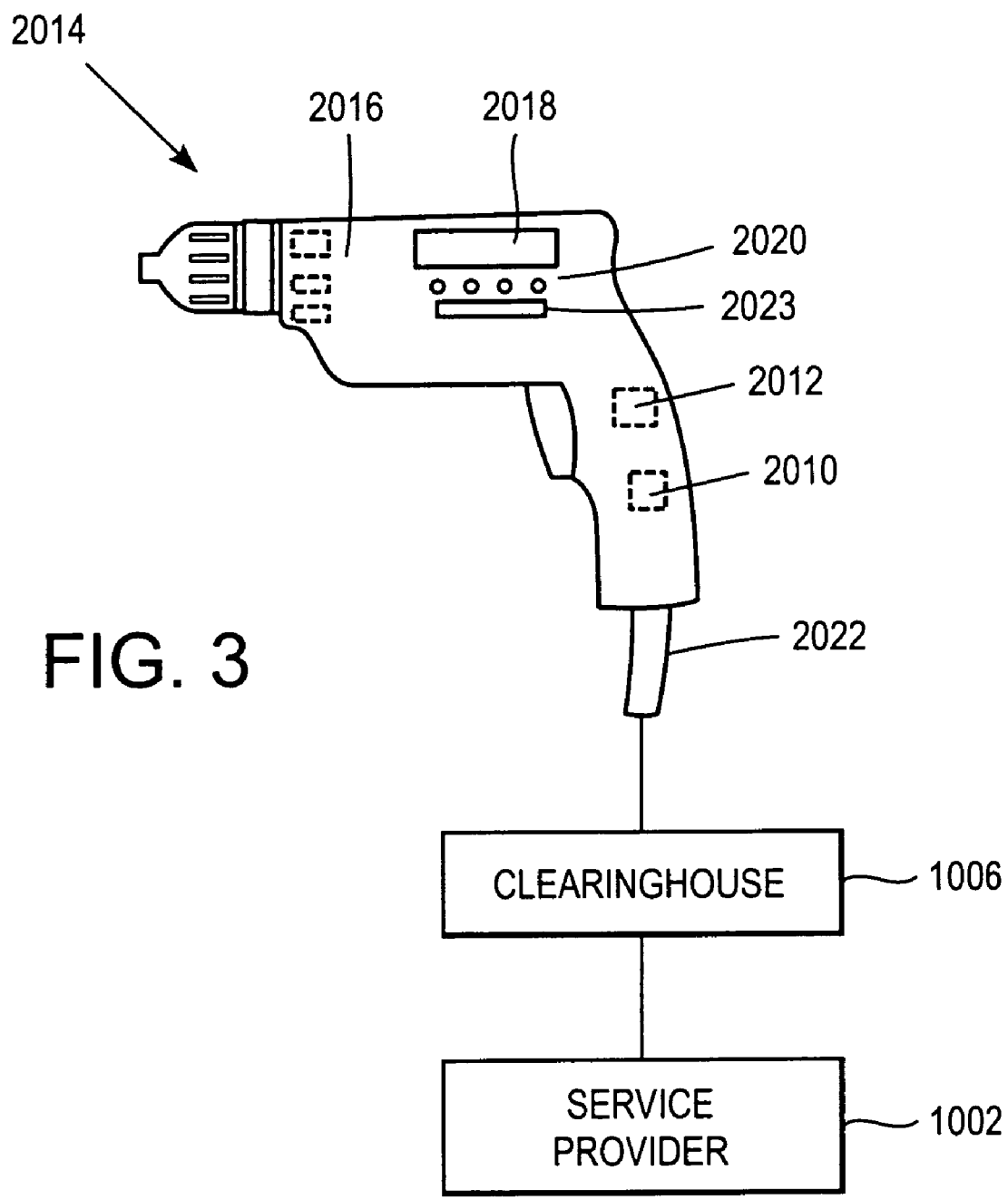
FIG. 3 is a side view of a power tool according to an embodiment of the invention.

The connection between the second network 1008 to the power tool 1014 may be through a communications device 1010 and a microprocessor 1012. In one embodiment of the invention, the communications device 1010 and the microprocessor 1012 are housed in a data management device (not shown in FIG. 1). In one aspect of this embodiment, the data management device is a handheld unit (discussed in more detail below). The communications device 1010 may be, for example, a modem. In other embodiments of the invention, the communications device 1010 and the microprocessor 1012 may be integral with the power tool 2014 (FIG. 3).

The modular microprocessor-base tool system 1000 may also include a memory 1013. This memory 1013 may also be integral with the power tool 1014 or located within the aforementioned handheld unit. Preferably the memory 1013 stores program instructions that aid in the operation of the power tool 1014 as well as coordinate the collection of data from sensors 1016a-1016c. Additionally, the memory can store sensor data and messages from the operator to the service provider 1002 and from the service provider 1002 to the operator.

Also depicted in FIG. 1 is an input mechanism 1020 and an output mechanism 1018. In one embodiment of the invention, the input mechanism a plurality of buttons or switches that allow the user to answer questions or input information related to the operation of the power tool 1014. Other input mechanisms may also be used. For example touch screens, light pens and miniature keyboards may also be used. Preferably, the output mechanism is a display screen that can display both text and graphics. However, audio output devices are also contemplated.

Associated with the power tool 1014 are sensors 1016a-1016c. As illustrated in FIG. 1, the power tool 1014 has three sensors 1016a-1016c. This is by way of example only. The power tool 1014 may have any number of sensors 1016. In one embodiment of the invention, the sensors 1016a-1016c are integral with the power tool 2014 (see FIG. 3). In other embodiments of the invention, one or more of the sensors 1016 may be external of the power tool 1014 but capable of measuring relevant data. For example, the one more external sensors 1016 may measure ambient temperature or relative humidity. In contrast, the internal sensor 1016 may be used to measure vibration, heat rate, temperature, torque, or any other useful property. The sensors 1016 are in signal communication with at least one of the microprocessor 1012 and the memory 1013.

Figure 2:
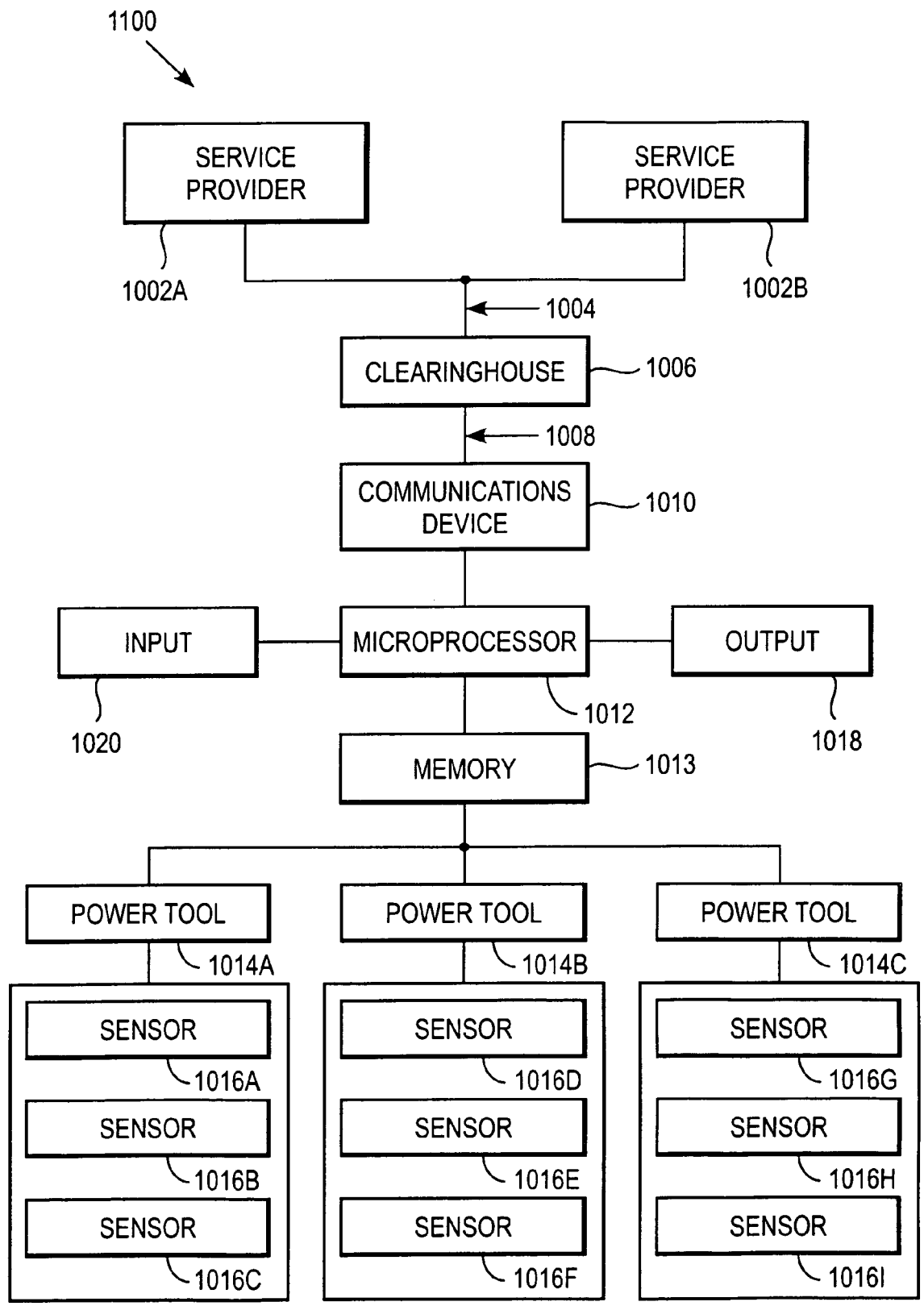
FIG. 2 is a schematic diagram of a power tool system according to another embodiment of the invention.

FIG. 2 illustrates another embodiment of the invention. The modular microprocessor-based power tool system 1100 of this embodiment may include more than one service provider 1002a, 1002b. As illustrated, there are two service providers 1002a, 1002b. However, there may be any number of service providers 1002.

As evident from the illustrated embodiment, the invention may include multiple power tools 1014a, 1014b, 1014c. FIG. 2 illustrates three power tools 1014a, 1014b, 1014c, however, any number of power tools 1014 may be included. This embodiment is suitable, for example, an industrial setting in which many power tools 1014 are in use. Each of the power tools 1014a, 1014b, 1014c has been illustrated with three sensors 1016a-1016c. As in the earlier embodiments, there may be more or less than three sensors per power tool 1014. Further, there may be any combination of service providers 1002, power tools 1014 and sensors 1016. The example illustrated in FIG. 2 for merely more illustrative purposes only.

FIG. 3 illustrates a power tool 2014 constructed according to one embodiment of the invention. In this embodiment, the power tool 2104 includes integral sensors 2016. Further, this embodiment includes an integral microprocessor 2012 and an integral communications device 2010. The integral communications device 2010 may be a modem or a wireless transmitter. In one aspect of the invention, the communications can be affected by sending a signal through the power cord 2022. In another aspect of the invention, a separate communications port (not shown) adapted to receive a communications cable can be provided. In still another aspect of the invention, the communications device 2010 is a wireless transmitter.

The power tool 2014 of this embodiment of the invention also includes a display 2018. Preferably, the display 2018 can illustrate graphics as well as alphanumeric text. The power tool 2014 may also include audible or tactile output devices (not shown). Also included are input devices 2020. As illustrated, input devices 2020 are push buttons. Alternative input devices 2020 include touch screens and switches. Further, it is contemplated that an entire miniature keyboard may be included. With the input device 2020, the power tool operator can respond to questions and comments from the service provider 1002 and even input questions for the service provider 1002. Thus, both data and messages can be sent back and forth from the power tool operator to the service provider 1002 via the clearinghouse 1006. The data may include "raw" data, that is, unanalyzed data. However, in some embodiments of the invention, the power tool 2014 is also provided with memory (not shown) and software that can analyze the sensor data. Thus, the service provider 1002 can be provided with both raw and analyzed data. In still other embodiments of the invention, the power tool 2014 is provided with a receptacle 2023 adapted to receive a program cartridge (not shown). In this embodiment, the program cartridge may include the instructions to adapt the power tool 2014 to operate in the power tool system. That is, the program cartridge may include instructions for operating the sensors 2016, the microprocessor 2012, the communications device 2010, the display 2018 and the input devices 2020.

In the preceding embodiments, and those that follow, it is possible to download the manufacturer's specifications from the network and/or record compliance with those specifications. The following is non-limiting example of one method of present invention illustrating a way of accomplishing this. In other embodiments of the method certain aspects may be omitted. In still other embodiments, additional aspects may be included. Further, the method need not be performed in the exact order presented herein but may be varied as desired by the user.

The tool 2014 queries the user for manufacturer, materials, or job information Manufacturer, materials, or job information is entered manually by user or through barcode scan or radio frequency identification tags The tool 2014 queries the central server and loads into the tool settings for a specific manufacturer, materials, or job specification The tool 2014 records and sends the users actions and sensor results to the central server for long term storage One example in which this method is advantageous is ensuring manufacturer torque specifications are being followed for wheel lug nuts for automobiles. Other examples include ensuring that fastening, cutting, and measurement specifications are met and monitored. Some of the benefits of the methods of the present invention include increased quality assurance, aiding less experienced workers to adhere to specifications, and recording results for quality and liability purposes.

There are many industrial applications and product and/or machine service and repair applications where the manufacturer or designer has precise specifications for how parts may be constructed, assembled, or fastened. In the automotive field, for example, every manufacturer has precise torque specifications for the lug nuts that fastening the wheels of the vehicle. Currently, service personnel look up the manufacturer specification for lug nut torque on a chart and are responsible for setting their torque wrenches so as not to under or over torque the nut. Because these specifications change from time to time with new makes and models of vehicles, it is difficult to ensure that workers always have the latest manufacturer information and that they are following best practices. Currently there is no effective way for manufacturers, customers, or supervisory personnel to ensure that service personnel are compliant with specifications.

With the methods of the present invention, service providers can enter into the system manufacturer information that is sent to the central server so that the current and most appropriate torque specifications can be automatically sent to the tool 2014 and loaded into the tool 2014 from the server. Preferably, the tool 2014 will always have access to the latest manufacturer specification for any available make or model. In addition, the tool 2014 can send to the server a record of the actual torque applied to the lug nuts so that the customer, manufacturer, and supervisor have a detailed record of torque associated with the service. This enables documentation for future liability protection. In the past, injurious automobile accidents have been blamed on improper torque being applied to lug nuts in routine automotive service, and lawsuits have resulted in millions of dollars of damages. Typically, there has not been, an accurate record of torque settings and compliance prior to this invention.

A similar need exists with many manufacturing processes in which power tools 2014 are used, especially in settings where the same power tool 2014 is used for multiple applications and can be adapted to the task at hand through program logic supplied from the server. For quality assurance and customer service, the same settings and results can be transmitted to the server for an accurate, long term record. This enables lesser skilled people to perform their jobs with higher skilled tools 2014.

In addition to torque specifications for nuts and other fastening applications, tool settings can be set from the server for cutting applications. The user can be queried about materials type, thickness and other properties so that the tool 2014 can be adjusted for cutting blade selection and blade rotation or speed. For other types of tools 2014 used, for example, for fastening or binding, materials properties can be equally important. These include, but are not limited to, force and depth on rivets or nails, or temperature settings on tools 2014 that use heat to fasten, solder, or bind parts and components.

Another case where specific information can be received from the server and where results can be stored on the server has to do with measurement. Examples include enabling accurate cutting lengths or depths, positioning of fasteners, positioning of components, height or depth of screws, or number of turns on a bolt. This information can be a result of the job that the user is working on, where specific step-by-step instructions are loaded into the tool based on the job or project. Specific actions may also be monitored and recorded, including the sensed result the user action, such as number of turns, cut length or depth, etc.

In still other embodiments of the invention, the microprocessor 1012 and the communications device 1010 are supplied in a separate unit (discussed in more detail below). In still other embodiments of the invention, the power tool user may connect the power tool 1014 to a personal computer (discussed in more detail below). The connection may be either direct or via the separate device. In this embodiment of the invention, the power tool user may take advantage of the keyboard and mouse of the personal computer to input information into the system.

Figure 4:
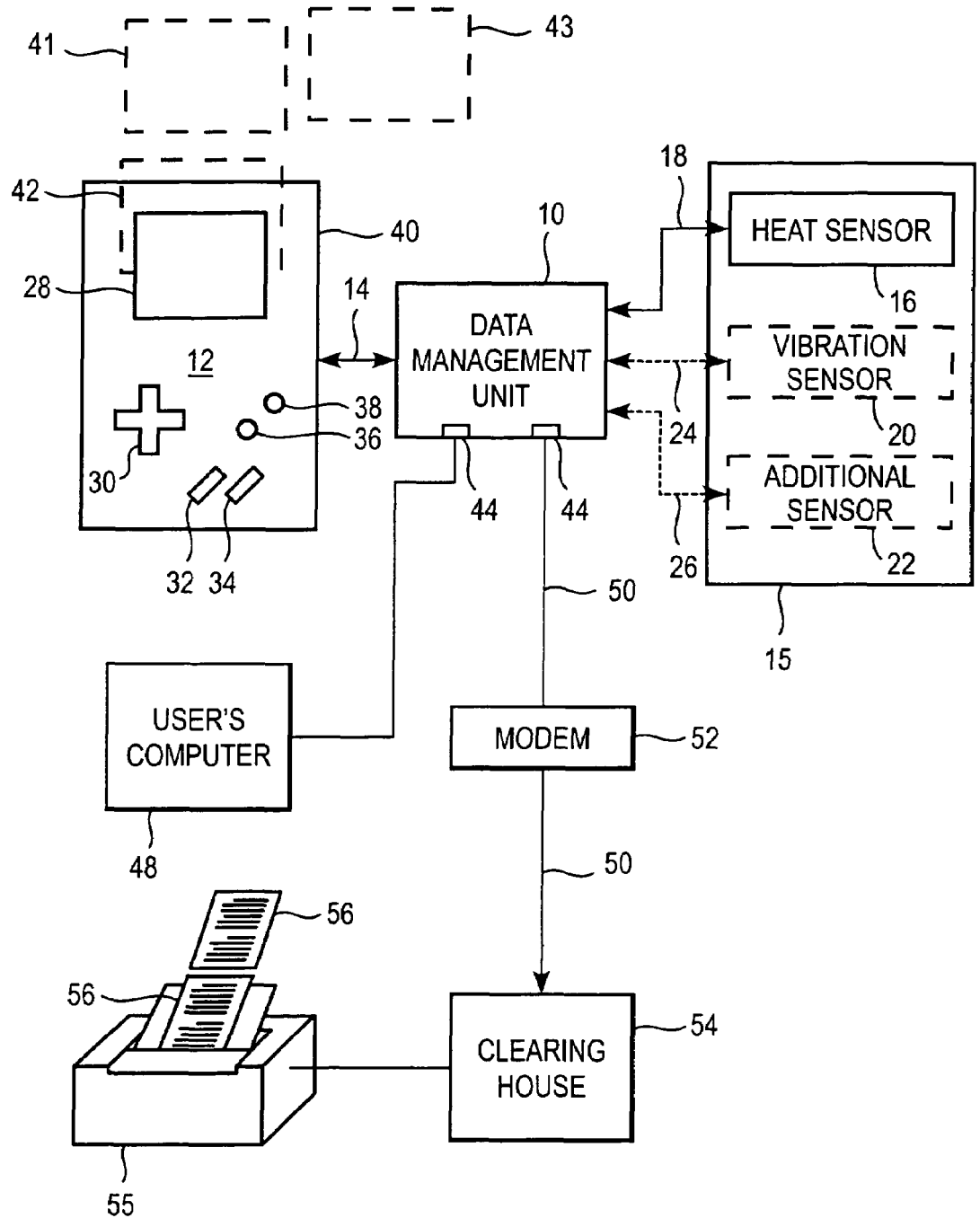
FIG. 4 is a schematic diagram of a power tool system according to an embodiment of the invention.

FIG. 4 depicts a modular microprocessor-based power tool system arranged in accordance with another embodiment of the invention. In the arrangement shown in FIG. 1, a data management device 10 is electrically interconnected with a handheld microprocessor-based device 12 via a cable 14. In the depicted arrangement, data management device 10 also is in signal communication with a power tool 15. The power tool 15 may have a heat sensor 16 capable of sensing heat generated by the power tool and producing an electrical signal representative thereof. Although FIG. 1 illustrates the power tool 15 as being connected to data management device 10 by a cable 18, it may be preferable to construct power tool 15 using wireless technology to provide signal communication between the power tool 15 and the data management device 10. Example wireless technologies include, but are not limited to, cell phone, RF, and Blue Tooth. Regardless of the manner in which power tool 15 is interconnected with data management device 10, both that interconnection and cable 14 can be configured for serial data communication between the interconnected devices. However, alternative date transfer schemes may be used.

Also shown in FIG. 4 are vibration sensor 20 and sensor 22, which are in data communication with data management device 10 via cables 24 and 26, respectively. Vibration sensor 20 and sensor 22 of FIG. 4 represent sensors other than heat sensor 16 that can be used with the invention. Additional properties that may be monitored by the sensors include, but are not limited to moisture, room temperature, location, direction, user identification, power, torque, motor jam, length and time of usage, cut distance, length of cut, equipment manufacturer information, equipment identification, and service record. Further, the sensors of the present invention are not limited for use with any particular power tool 16. For example, the power tool 16 may be a drill, saw, sander, grinder, router, or joiner; or outdoor tools such as lawn mowers and hedge trimmers; or construction tools such as jack hammers. Upon understanding the various aspects and features of the invention it will be recognized that the invention is easily implemented for industrial as well as home or commercial use. Further, multiple sensors may be used with any given power tool 16 and multiple power tools 16 may be simultaneously monitored by the system. Sensors used in the practice of the invention can be arranged in a variety of ways. The data to be recorded or otherwise employed by handheld microprocessor device 12 and/or data management device 10 can be provided in serial format in synchronization with clock signals provided by data management device 10. The sensors can be connected to data management device 10 with cables (as shown in FIG. 4) or may be connected via wireless technology.

As is shown in FIG. 4, handheld microprocessor device 12 may include a display screen 28 and at least one input mechanism such as a plurality of switches or keys (30, 32, 34, 36, and 38 in FIG. 4), which are mounted on a housing 40. Located in the interior of housing 40, but not shown in FIG. 4, are a microprocessor, memory circuits, and circuitry that interface with switches 30, 32, 34, 36 and 38 with the microprocessor. Stored in the memory of program handheld microprocessor device 12 can be a set of program instructions that establishes a data protocol that allows handheld microprocessor device 12 to perform digital data signal processing and generate desired data or graphics for display on display 28 when a program cartridge 42 is inserted in a slot or other receptacle in housing 40. That is, program cartridge 42 of FIG. 4 may include read-only memory units (or other memory means such as battery-powered random access memory) which store program instructions and data that adapt handheld microprocessor 12 for operation in modular microprocessor-based power tool system. More specifically, when the instructions and data of program cartridge 42 are combined with program instructions and data included in the internal memory circuits of handheld microprocessor device 12, handheld microprocessor device 12 is programmed for processing and displaying power tool operational information in the manner described below. In each case, the plurality of switches or keys (30, 32, 34, 36, and 38 in FIG. 4) are selectively operated to provide signals that result in pictorial and/or alphanumeric information being displayed by display 42.

Various devices are known that meet the above-set forth description of handheld microprocessor device 12. For example, compact devices are available in which the plurality of keys allows alphanumeric entry and internal memory can be provided for storing information such as names, addresses, phone numbers, and an appointment calendar. Small program cartridges or cards can be inserted in these devices to program the device for various purposes such as the playing of games, spreadsheet application, and foreign language translation sufficient for use in travel. More recently, less compact products that have more extensive computational capability and are generally called "palm top computers" have been introduced into the marketplace. These devices also can include provision for programming the device by way of an insertable program card or cartridge. Alternatively, a handheld microprocessor device 12 can be provided with an internal memory (not removable) containing the necessary program instructions.

Certain embodiments of the invention are configured and arranged to operate in conjunction with yet another type of handheld microprocessor unit. Specifically, in these embodiments of the invention, program cartridge 42 is electrically and physically compatible with commercially available compact video game systems, such as the system manufactured by Nintendo of America Inc. under the trademark "GAME BOY." Configuring data management device 10 and program cartridge 42 for operation with a handheld video game system has several advantages. For example, the display of such a device provides display resolution that allows the invention to display both multi-line alphanumeric information and graphical data. In this regard, the 160×144 pixel dot matrix-type liquid crystal display screen currently used in the above-referenced compact video game systems provides sufficient resolution for at least six lines of alphanumeric text, as well as allowing graphical representation of statistical data such as graphical representation of heat or vibration generated by the power tool 15.

Another advantage of providing handheld microprocessor device 12 in the form of a compact video game system is the relatively simple, yet versatile arrangement of switches that is provided by such a device. For example, as is indicated in FIG. 4, a compact video game system includes a control pad 30 that allows an object displayed on display 42 to be moved in a selected direction (i.e., up-down or left-right). As also is indicated in FIG. 4, compact video game systems typically provide two pair of distinctly shaped push button switches. In the arrangement shown in FIG. 4, a pair of spaced-apart circular push button switches (36 and 38) and a pair of elongate switches (32 and 34) are provided. The functions performed by the two pairs of switches is dependent upon the program instructions contained in each program cartridge 42. The device illustrated in FIG. 4 is but one commercially available device. Any commercially available or proprietarily designed device having an alternative arrangement of buttons may be used.

Yet another advantage of utilizing a compact video game system for handheld microprocessor-based device 12 of FIG. 4 is the widespread popularity and low cost of such units. In this regard, manufacture and sale of a data management device 10, power tool 15 with sensor 16 and program cartridge 42 that operate in conjunction with a compact microprocessor-based video system allows the modular microprocessor-based power tool system of FIG. 4 to be manufactured and sold at a lower cost than could be realized in an arrangement in which handheld device 12 is designed and manufactured solely for use in the system of FIG. 4.

Another advantage of utilizing a compact video game system for handheld microprocessor-based device 12 of FIG. 4 is that power tools are increasingly being designed for children and used by children at home, as both toys and as child-versions of adult tools for construction and play. Integrating educational instructions, monitoring and feedback using a game system enables the least skilled users of power tools to gain skills by learning to use tools for a variety of projects that can be loaded into the data management device 10 from the network or inserted with a program cartridge 42.

An even further advantage of using a compact video game system for handheld microprocessor 12 is that such video game systems include means for easily establishing the electrical interconnection provided by cable 14 in FIG. 4. In particular, such compact video game systems include a connector mounted to the game device housing (40 in FIG. 4) and a cable that can be connected between the connectors of two video game units to allow interactive operation of the two interconnected units (i.e., to allow contemporaneous game play by two players or competition between players as they individually play identical but separate games). In certain embodiments of the invention, the "two-player" cable supplied with the compact video game device being used as handheld microprocessor device 12 is used as cable 14 to establish serial data communication between the handheld microprocessor device 12 (compact video game system) and data management device 10. In these embodiments, the program instructions stored on the memory of data management device 10 and program cartridge 42 respectively program data management device 10 and the compact video game system (i.e., handheld microprocessor device 12) for interactive operation in which switches 30, 32, 34, 36 and 38 are used to control the operation of data management device 10 (e.g., to select a particular operational mode such as determining the optimal location of a cut or the display of statistical test data and, in addition, to control operation such as selection of an option during operation of the system in a particular operational mode). In each operational mode, data management device 10 processes data in accordance with program instructions stored in the memory circuits of data management device 10. Depending upon the operational mode selected by the user, data is supplied to data management device 10 by sensor 16, by additional sensors (20 and 22 in FIG. 4) or any interconnected computers or data processing facility (such as the hereinafter described user's computer 48 and clearinghouse 54 of FIG. 4). During such operation, mode switches 30, 32, 34, 36 and 38 are selectively activated so that signals are selectively coupled to the video game system (handheld microprocessor device 12) and processed in accordance with program instructions stored in program cartridge 42. The signal processing performed by handheld microprocessor device 12 results in the display of alphanumeric, symbolic, or graphic information on the video game display screen (i.e., display 28 in FIG. 4), which allow the user to control system operation and obtain desired test results and other information.

With continued reference to FIG. 4, a data management device 10 of the invention may include a data port 44 that allows communication between data management device 10 and a personal computer 48 (or other programmable data processor). In certain embodiments of the invention, data port 44 is an RS-232 connection that allows serial data communication between data management device 10 and personal computer 48. In the practice of the invention, personal computer 48 can be used to supplement data management device 10 by, for example, performing more complex analyses of vibration and other data that has been supplied to and stored in the memory circuits of data management device 10. Alternatively, personal computer 48 can be used to supply data to data management device 10 that is not conveniently supplied by using handheld microprocessor switches 30, 32, 34, 36 and 38 as an operator interface to the system shown in FIG. 4. For example, some embodiments of the invention may employ a substantial amount of alphanumeric information that must be entered by the system user. Although it is possible to enter such data by using switches 30, 32, 34, 36 and 38 in conjunction with menus and selection screens displayed on display screen 28 of FIG. 4, it may be more advantageous to use a device such as personal computer 48 for entry of such data. However, if personal computer 48 is used in this manner, some trade-off of system features may be required because data management device 10 must be temporarily interconnected with personal computer 48 during these operations. That is, some loss of system mobility might result because a suitably programmed personal computer would be needed at each location at which data entry or analysis is to occur.

As is indicated in FIG. 4, a data management device 10 of the invention may also include a modem 52 that allows data communication between data management device 10 and a remote computing facility identified in FIG. 4 as clearinghouse 54 via a conventional telephone line (indicated by reference numeral 50 in FIG. 4) or by a wireless network. As shall be described in more detail, clearinghouse computing facility 54 facilitates communication between a user of the system shown in FIG. 4 and professional service provider and can provide additional services such as updating system software. As is indicated by facsimile machine 55 of FIG. 4, one optional function of clearinghouse 54 is providing the professional service provider with standardized reports 56, which indicate both the current condition and condition trends of the system user. Although a single facsimile machine 55 is shown in FIG. 4, it will be recognized that numerous service providers (and hence facsimile machine 55) can be connected in signal communication with a clearinghouse 54.

Regardless of whether a compact video game system, another type of commercially available handheld microprocessor-based unit, a specially designed microprocessor device, or a microprocessor device integral with the power tool 15, is used, embodiments of a modular microprocessor-based power tool system according to the present invention: (a) adapts a microprocessor device for displaying instructions for performing the monitoring and/or controlling a power tool 15; (b) adapts a microprocessor device for displaying (graphically or alphanumerically) statistical data such as heat or vibration; (c) adapts a microprocessor device for supplying control signals and signals representative room temperature, scaling factors or other useful information, optionally to data management device 10; (d) adapts a microprocessor device for simultaneous graphical display of cut locations with information such as saw speed; and, (e) adapts a microprocessor device for displaying information or instructions from a service provider that may be coupled to data management device 10 from a clearinghouse 54. The manner in which the arrangements of the present invention implement the above-mentioned functions and others can be better understood with reference to the illustrative embodiments of FIGS. 5 and 6.

Figure 5:
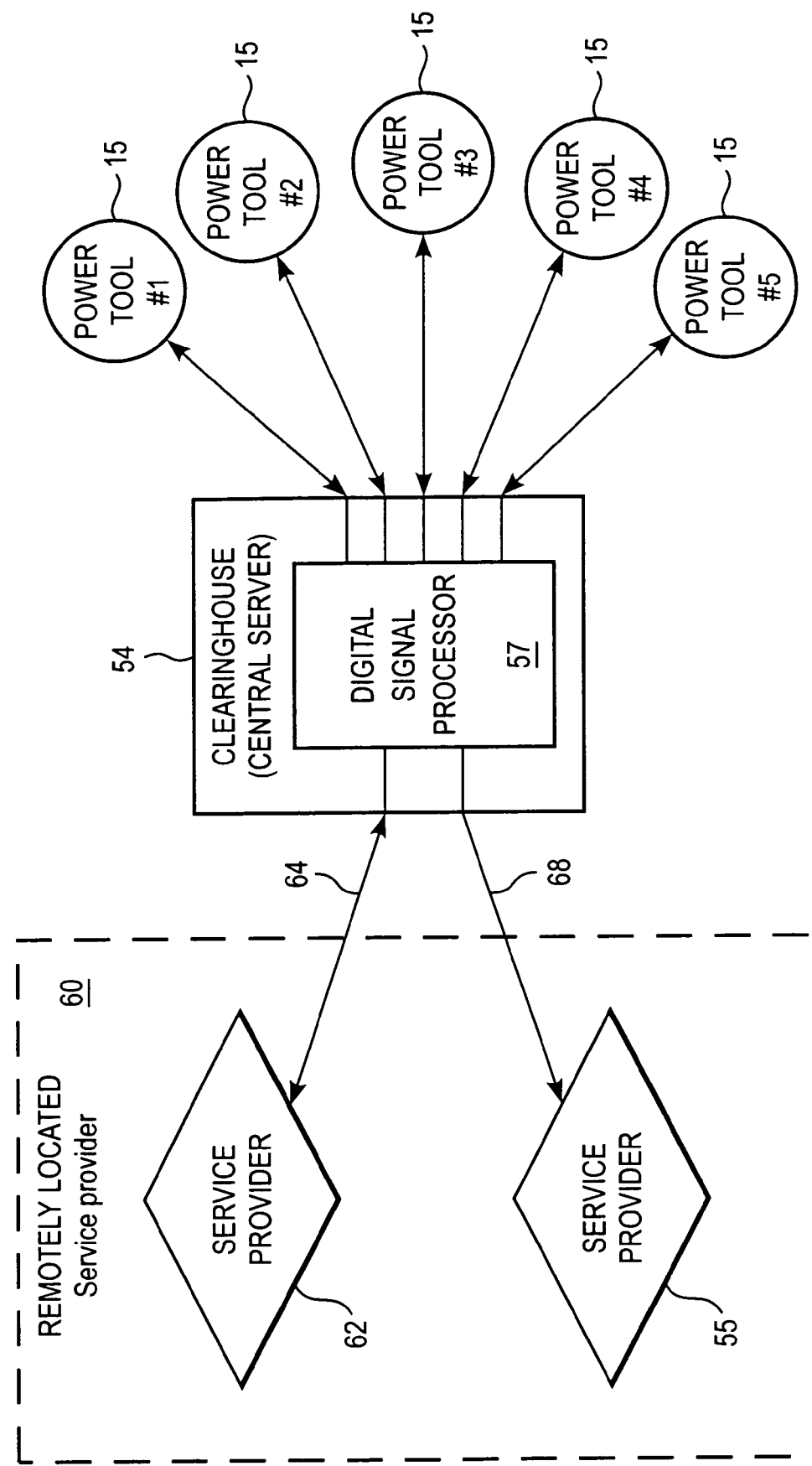
FIG. 5 is a schematic diagram of a power tool system according to another embodiment of the invention.

Referring first to FIG. 5, clearinghouse 54 receives data from one or more modular microprocessor-based power tools 15 of the type shown in FIG. 4. The data supplied to clearinghouse 54 by each individual modular microprocessor-based power tool 15 may comprise "raw data," i.e., a parameter associated with the operation of the power tools 15 and related data that may be stored in memory circuits of the microprocessor device or a data management device 10, without further processing. For example, with respect to the arrangement shown in FIG. 4, heat and/or vibration and associated data such as room temperature and other such conditions are transmitted to clearinghouse 54 and stored with a digitally encoded signal that identifies both the source of the information (i.e., the power tool) and those having access to the stored information (i.e., the system user's service providers).

As shall be recognized upon understanding the manner in which it operates, clearinghouse 54 can be considered to be a central server for the various system users and each service provider 60. In that regard, clearinghouse 54 includes conventionally arranged and interconnected digital processing equipment (represented in FIG. 5 by digital signal processor 57) which receives digitally encoded information from a user or service provider 60; processes the information as required; stores the information (processed or unprocessed) in memory if necessary; and, transmits the information to an intended recipient (i.e., user or service provider 60).

In FIG. 5, rectangular outline 60 represents one of numerous remotely located service providers who can utilize clearinghouse 54 and the arrangement described relative to FIGS. 1 and 2 in monitoring and controlling power tool programs. Shown within outline 60 is a computer 62 (e.g., personal computer), which is coupled to clearinghouse 54 by means of a modem (not shown in FIG. 2) and a telephone line 64 or wireless network (not shown). Also shown in FIG. 5 is the previously mentioned facsimile machine 55, which is coupled to clearinghouse 54 by means of a second telephone line 68 or wireless network (not shown). Using the interface device of computer 62 (e.g., a keyboard or pointing device such as a mouse), the service provider can establish data communication between computer 62 and clearinghouse 54. Once data communication is established between computer 62 and clearinghouse 54, power tool information can be obtained from clearinghouse 54 in a manner similar to the manner in which subscribers to various database services access and obtain information. In particular, the service provider can transmit an authorization code to clearinghouse 54 that identifies the service provider as an authorized user of the clearinghouse and, in addition, can transmit a signal representing the power tool for which power tool information is being sought. As is the case with conventional database services and other arrangements, the identifying data is keyed into computer 62 by means of a conventional keyboard (not shown in FIG. 5) in response to prompts that are generated at clearinghouse 54 for display by the display of computer 62 (not shown in FIG. 5).

Depending upon the hardware and software arrangement of clearinghouse 54 and selections made by the service provider via computer 62, power tool information can be provided to the service provider in different ways. For example, computer 62 can be operated to access data in the form that it is stored in the memory circuits of clearinghouse 54 (i.e., raw data that has not been processed or altered by the computational or data processing arrangements of clearinghouse 54). Such data can be processed, analyzed, printed and/or displayed by computer 62 using commercially available or custom software. On the other hand, various types of analyses may be performed by clearinghouse 54 with the results of the analyses being transmitted to the remotely located service provider 60 and/or system user. For example, clearinghouse 54 can process and analyze data in a manner identical to the processing and analysis provided by the power tool system of FIG. 5. With respect to such processing and any other analysis and processing provided by clearinghouse 54, results expressed in alphanumeric format can be sent to computer 62 via telephone line 64 and the modem associated with computer 62, with conventional techniques being used for displaying and/or printing the alphanumeric material for subsequent reference.

The arrangement of FIG. 5 also represents one possible arrangement that allows the service provider to send messages and/or instructions to each power tool 15 via computer 62, telephone line 64, and clearinghouse 54. The messages may be educational or may include feedback to the user as to how the power tool is performing. In particular, clearinghouse 54 can be programmed to generate a menu that is displayed by computer 62 and allows the service provider to select a mode of operation in which information is to be sent to clearinghouse 54 for subsequent transmission to a user of the system described relative to FIGS. 1-4. This same menu (or related submenus) can be used by the service provider to select one or more modes of operation of the above-described type in which either unmodified power tool data or the results of data that has been analyzed by clearinghouse 54 is provided to the service provider via computer 62 and/or facsimile machine 55.

In the contemplated embodiments of the present invention the user of the power tool 15 can be provided with messages or instructions such as step-by-step instructions, tool positioning for an upcoming cut, a laser guide cut length, a record of successful cuts, a list of upcoming cuts, project design, scaling factors, a materials list, a cut list, wood or materials type, equipment information or other aspects of the power tool program. Transmitting messages is similar to the operation that allows the service provider to access data sent by a power tool, i.e., transmitted to clearinghouse 54. The process differs in that the service provider 60 enters or selects the desired message or instruction via the keyboard or other interface device of computer 62. Once the message or instruction is entered and transmitted to clearinghouse 54, it is stored for subsequent transmission to the user for whom the information or instruction is intended. It should be understood that it is within the scope of the present invention that such messages or instructions can compromise a number of standard pre-composed messages or instructions that can be manually or automatically selected from a menu or list. These standard messages or instructions can optionally be selected based, at least in part, on the data collected from the power tool 15. For example, based on the project design and the scaling factors, a materials and cut list may be generated for the end user.

Based on the equipment and materials, settings are set to server and are then transmitted directly to the tool or via the handheld microprocessor unit 12 and/or the data management device 10.

With respect to transmitting stored messages or instructions to a user of the invention, at least two techniques are available. The first technique is based upon the manner in which operational modes are selected in the practice of the invention. Specifically, in certain embodiments of the invention, program instructions that are stored in memory cause the system to generate menu screens which are displayed. The menu screens allow the system user to select the basic mode in which the system of is to operate and, in addition, allow the user to select operational subcategories within the selected mode of operation. Various techniques are known to those skilled in the art for displaying and selecting menu items. For example, in the practice of this invention, one or more main menus can be generated and displayed which allow the system user to select operational modes that may include: (a) a monitor mode (e.g., monitoring of heat generation); (b) a display mode (e.g., displaying previously obtained heat generation results, the service record, or other relevant information); (c) an input mode (e.g., a mode for entering data such as providing information that relates to the materials to be cut, fastener type (screw or nail), finish desired, etc., or even answering survey questions); and, (d) a communications mode (for establishing a communication link with a remote computing facility such as clearinghouse 54 of FIG. 4).

In embodiments of the invention that employ a compact video game system for a handheld microprocessor device 12, the selection of menu screens and the selection of menu screen items preferably can be accomplished in substantially the same manner as menu screens and menu items are selected during the playing of a video game. For example, the program instructions stored in data management device 10 and program cartridge 42 of the arrangement of FIG. 4 can be established so that a predetermined one of the compact video game switches (e.g., switch 32 in FIG. 4) allows the system user to select a desired main menu in the event that multiple main menus are employed. When the desired main menu is displayed, operation by the user of control pad 30 allows a cursor or other indicator that is displayed on the menu to be positioned adjacent to or over the menu item to be selected. Activation of a switch (e.g., switch 36 of the depicted handheld microprocessor device 12) causes the handheld microprocessor device 12 and/or data management device 10 to initiate the selected operational mode or, if selection of operational submodes is required, causes handheld microprocessor device 12 to display a submenu.

In view of the above-described manner in which menus and submenus are selected and displayed, it can be recognized that arrangements of the present invention can be configured and arranged to display a menu or submenu item that allows the user to obtain and display messages or instructions that have been provided by a service provider and stored in clearinghouse 54. For example, a submenu that is generated upon selection of the previously mentioned communications mode can include submenu items that allow the user to select various communication modes, including a mode in which serial data communication is established with clearinghouse 54, and a message status request is transmitted to clearinghouse 54. When this technique is used, the data processing system of clearinghouse 54 is programmed to search the clearinghouse memory to determine whether a message exists for the user making the request. Any messages stored in memory for that user are then transmitted to the user and processed for display or other output device. If no messages exist, clearinghouse 54 transmits a signal that causes the display or other output device to indicate "no messages." In this arrangement, clearinghouse 54 preferably is programmed to store a signal indicating that a stored message has been transmitted to the intended recipient (user). Storing such a signal allows the service provider to determine that messages sent to clearinghouse 54 for forwarding to a power tool user have been transmitted to that power tool user. In addition, program instructions allow the system user to designate whether received messages and instructions are to be stored in the memory for subsequent retrieval or review. In addition, in some instances it may be desirable to program clearinghouse 54 so that the service provider can designate (i.e., flag) information such as changes in operating conditions that will be prominently displayed to the user (e.g., accompanied by a blinking indicator) and stored in the memory regardless of whether the system user designates the information for storage. In still other instances, the system user inputs data associated with the materials he is using, such as the length and thickness of a particular board, and the service provider (or a program on the clearinghouse server) determines the optimal locations for cutting, drilling of holes, placement of fasteners, and the like. Further, the system user may input data associated with materials and the particular power tool 15 and the service provider (or a program on the clearinghouse server) determines the appropriate settings for operation of the power tool 15.

A second technique that can be used for forwarding messages or instructions to a user does not require the system user to select a menu item requesting transmission by clearinghouse 54 of messages that have been stored for forwarding to that user. In particular, clearinghouse 54 can be programmed to operate in a manner that either automatically transmits stored messages for that user when the user operates the system or programmed to operate in a manner that informs the user that messages are available and allows the user to access the messages when he or she chooses to do so.

Practicing the invention in an environment in which the service provider uses a personal computer in some or all of the above-discussed ways can be very advantageous. On the other hand, the invention may also provide service providers timely information about system users without the need for a computer or any equipment other than a conventional facsimile machine (55 in FIGS. 4 and 5), or similar output device capable of receiving signals over a wired or wireless network, and presenting the information to the service provider. For example, information provided to clearinghouse 54 by a system user 15 can be sent to a service provider 60 via telephone line 68 and facsimile machine 55, with the information being formatted as a standardized graphic or textual report (56 in FIG. 4). Formatting a standardized report 56 (i.e., analyzing and processing data supplied by power tool 16 or other system monitor or sensor) can be effected either by data management device 10 or within the clearinghouse facility 54. Moreover, various standardized reports can be provided. Preferably, the signal processing arrangement included in clearinghouse 54 allows each service provider 60 to select which of several standardized reports will be routinely transmitted to the service providers' facsimile machine 55 or other output device, and, to do so on a power tool-by-power tool (user-by-user) basis.

Figure 6:
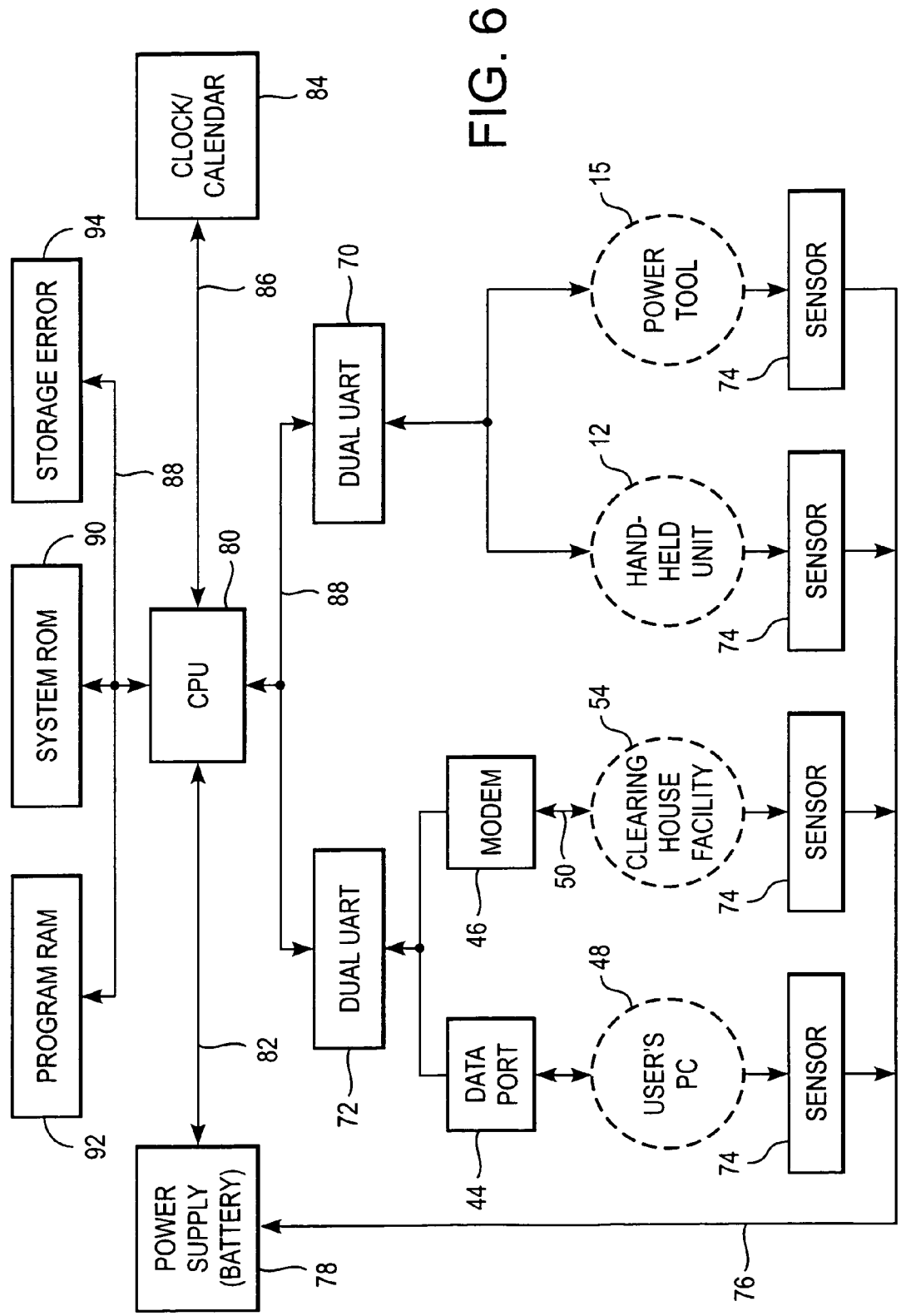
FIG. 6 is a schematic diagram illustrating structural components of a data management device and its connection to other components of the power tool system.

FIG. 6 illustrates one embodiment of a manner in which various system components are arranged and interconnected with other system components for affecting the above-described operational aspects of the invention. As is symbolically indicated in FIG. 6, microprocessor device 12 and power tool 15 are electrically connected to a dual universal asynchronous receiver transmitter 70 (by any suitable means such as cables 14 and 18). As also is indicated in FIG. 4 when a system user connects a personal computer 48 (or other programmable digital signal processor) to data port 44, signal communication is established between personal computer 48 and a second dual universal asynchronous receiver transmitter 72. Additionally, dual universal asynchronous receiver transmitter 72 is coupled to a communications device such as a modem 46 so that data communication can be established with a remote clearinghouse 54.

One embodiment includes a plurality of signal sensors 74, with at least one individual signal sensor being associated with each device. As previously discussed, and as is indicated in FIG. 6, these devices may include handheld microprocessor device 12, power tool 15, personal computer 48, remote computing facility 54 and, in addition, other additional power tools 15. Each signal sensor 74 is electrically connected for receiving a signal that will be present when the device with which that particular signal sensor is associated therewith and, in addition, is energized (e.g., turned on). For example, in previously mentioned embodiments of the invention in which data port 44 is an RS-232 connection, the signal sensor 74 that is associated with personal computer 48 can be connected to an RS-232 terminal that is supplied power when a personal computer is connected to data port 44 and the personal computer is turned on. In a similar manner, the signal sensor 74 that is associated with clearinghouse 54 can be connected to modem 46 so that the signal sensor 74 receives an electrical signal when modem 46 is interconnected to a remote computing facility (e.g., clearinghouse 54 of FIG. 5) via a telephone line 50.

In the arrangement of FIG. 6, each signal sensor 74 is preferably a low power switch circuit (e.g., a metal-oxide semiconductor field-effect transistor circuit), which automatically energizes data management device 10 whenever any one (or more) of the devices are associated with signal sensors 74 and is energized. Thus, as is indicated in FIG. 6 by signal path 76, each signal sensor 74 is interconnected with power supply 78, which supplies operating current and typically consists of one or more small batteries (e.g., three AAA alkaline cells).

The microprocessor and other conventional circuitry that enables processing system signals in accordance with stored program instructions is indicated in FIG. 6 by a programmable microprocessor or central processing device (CPU) 80. As is indicated in FIG. 6 by interconnection 82 between CPU 80 and battery 78, CPU 80 receives operating current from power supply 78, with power being provided only when one or more of the signal sensors 74 are activated in the previously described manner. A clock/calendar circuit 84 is connected to CPU 80 (via signal path 86 in FIG. 6) to allow time and date tagging of service tests and other information. Although not specifically shown in FIG. 6, operating power is supplied to clock/calendar 84 at all times.

In operation, CPU 80 receives and sends signals via a data bus (indicated by signal path 88 in FIG. 6), which interconnects CPU 80 with dual universal asynchronous receiver transmitters 70 and 72. The data bus 88 also interconnects CPU 80 with memory circuits, which, in the depicted embodiment, include a system read-only memory (ROM) 90, a program random access memory (RAM) 92, and an electronically erasable read-only memory (EEROM) 94. System ROM 90 can store program instructions and any data required for programming. During operation of the system, program RAM 92 provides memory space that allows CPU 80 to carry out various operations that are required for sequencing and controlling the operation of the system. In addition, RAM 92 can provide memory space that allows external programs (e.g., programs provided by clearinghouse 54) to be stored and executed. EEROM 94 allows test results and other data information to be stored and preserved until the information is no longer needed (i.e., until purposely erased by operating the system to provide an appropriate erase signal to EEROM 94).

In other embodiments of the invention, all or a portion of the functions and operations attributed to data management device 10 and/or handheld microprocessor device 12 can be performed by components or mechanisms such as a microprocessor located in the power tool 15. In addition, the power tool 15 may include microprocessor circuitry for generating visual display signals and signals representative of both current and past values of sensed parameters or even the service record of the power tool 15. Conventional programming and design techniques can be employed to adapt commercially available units for the performance of the various functions and operations of data management device 10 and/or the handheld device 12. In arrangements in which the power tool 15 includes a microprocessor that is programmed to provide signal processing in the above-described manner, the invention can use a signal interface device similar to those described above. That is, depending upon the amount of signal processing effected by the power tool and the amount of signal processing performed by a microprocessor of programmable handheld device 12 (if present), the signal interface required ranges from a conventional cable (e.g., interconnection of RS232 ports) to an arrangement in which signal communication is provided with an internal or external modem, or an arrangement in which the signal interface provides only a portion of the signal processing described relative to FIGS. 4-5. Further, in another aspect of this embodiment of the invention, the display may also be integrated into the power tool 15.

The invention also is capable of transmitting information to a remote location (e.g., clearinghouse 54 and/or a remotely located service provider) by means other than conventional telephone lines. For example, a modem that is configured for use with a cellular telephone system can be employed to transmit the signals provided by the modular microprocessor-based power tool system to a remote location via modulated RF transmission. Moreover, the invention can be employed with various digital networks such as recently developed interactive voice, video and data systems such as television systems in which a television and user interface apparatus is interactively coupled to a remote location via coaxial or fiberoptic cable and other transmission media.

Figure 7:
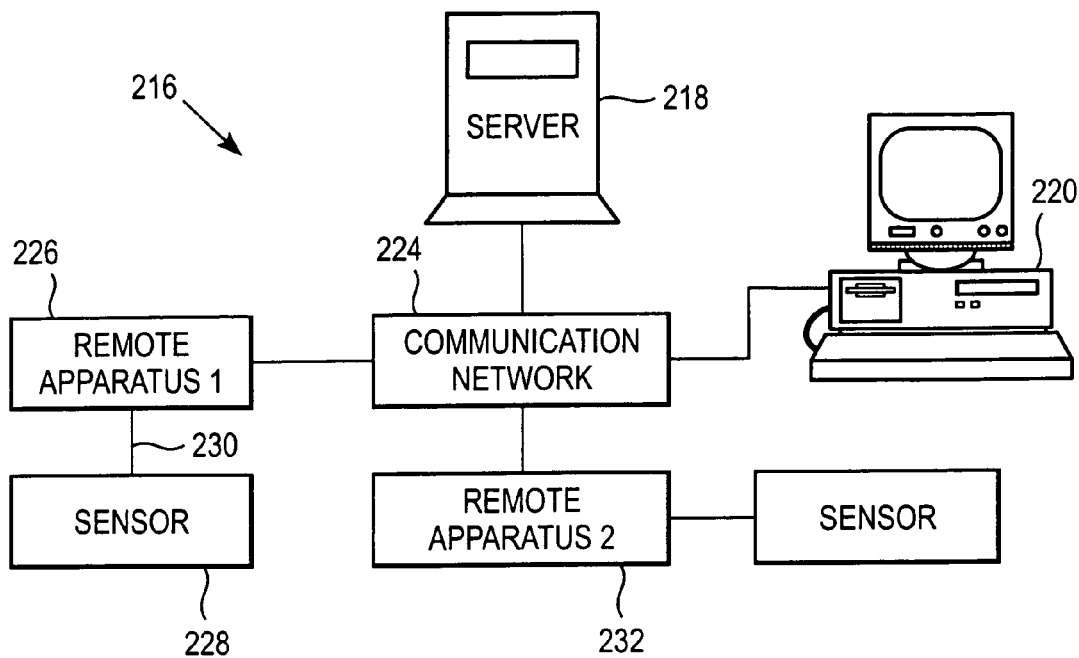
FIG. 7 is a schematic diagram of a power tool system according to an alternate embodiment of the invention.

Another embodiment of the invention is illustrated in FIGS. 7-17. Referring to FIG. 7, a networked system 216 includes a server 218 and a workstation 220 connected to server 218 through a communication network 224. Server 218 is preferably a world wide web server and communication network 224 is preferably the Internet. It will be apparent to one skilled in the art that server 218 may comprise a single stand-alone computer or multiple computers distributed throughout a network. Workstation 220 is preferably a personal computer, remote terminal, or web TV device connected to server 218 via the Internet. Workstation 220 functions as a remote interface for entering or selecting in server 218 messages and queries to be communicated to the power tools.

System 216 may also include first and second remotely programmable apparatuses 226 and 232 for use with first and second power tools, respectively. Each apparatus 226/232 is designed to interact with a power tool in accordance with script programs received from server 218. Each apparatus 226/232 is in communication with server 218 through communication network 224, preferably the Internet. Alternatively, each apparatus 226/232 may be placed in communication with server 218 via wireless communication networks, cellular networks, telephone networks, or any other network which allows each apparatus 226/232 to exchange data with server 218. For clarity of illustration, only two apparatuses 226 and 232 are shown in FIG. 7. It is to be understood that system 216 may include any number of remotely programmable apparatuses for monitoring any number of power tools.

In one embodiment, each power tool to be monitored is also provided with a sensor 228. Sensor 228 is designed to produce measurements of a parameter associated with the operation of the power tool, record the measurements, and transmit the measurements to the remotely programmable apparatus 226/232 through a standard connection cable 230 as described above. Alternatively, measurements can be transmitted to the apparatus 226/232 via a wireless interface or transmission media. Examples of suitable sensors 228 include heat, vibration, moisture, room temperature, location, direction, user identification, power, torque, motor jam, length and time of usage, cut distance, length of cut, equipment manufacturer information, equipment identification, or service record. Such sensors 228 are well known in the art. The specific type of sensor 228 provided to each power tool is dependent upon the need of the operator. For example, a torque sensor may be supplied to power tool for tightening bolts to prevent over-torquing of the bolt.

Figure 8:
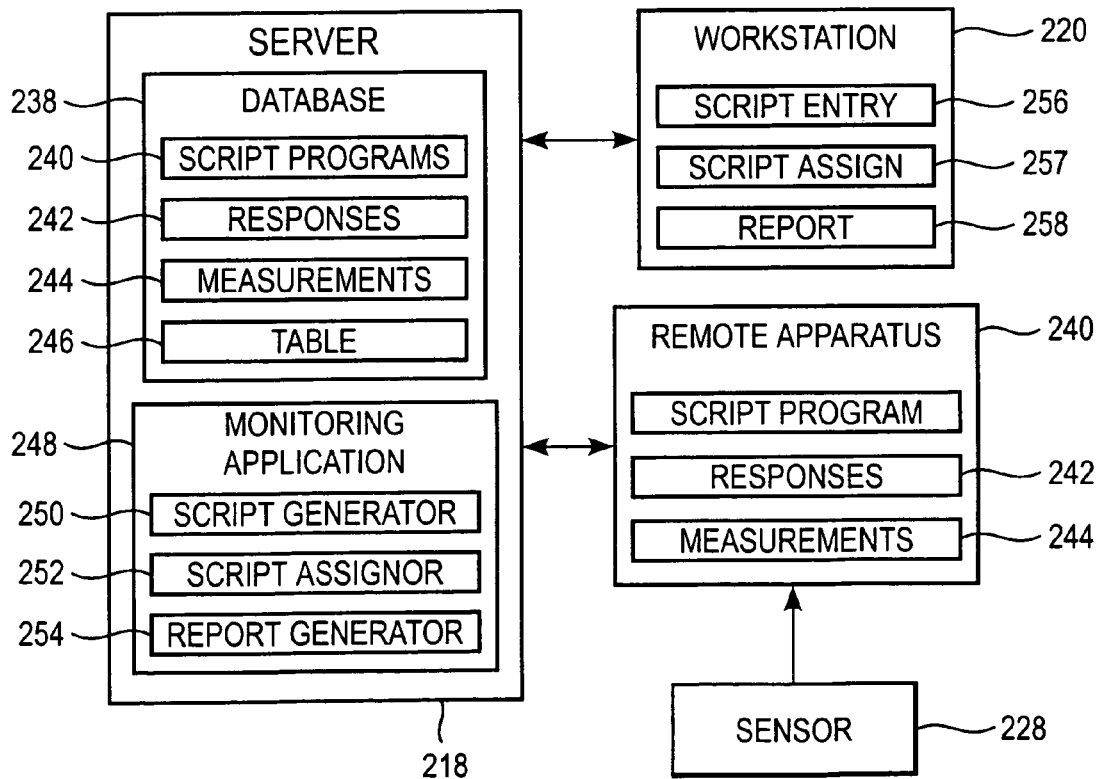
FIG. 8 is a schematic diagram illustrating the interaction of components of the embodiment of FIG. 7

FIG. 8 shows server 218, workstation 220, and apparatus 226 in greater detail. Server 218 includes a database 238 for storing script programs 240. Script programs 240 are executed by each apparatus e.g., 226/232, to communicate queries and messages to a power tool operator, receive responses 242 to the queries, collect measurements 244, and to transmit responses 242 and measurements 244 to server 218. Database 238 is designed to store responses 242 and measurements 244. Database 238 further includes a look-up table 246. Table 246 contains a list of the power tools to be monitored, and for each power tool, a unique power tool identification code and a respective pointer to the script program assigned to the power tool. Each remotely programmable apparatus, e.g., 226/232, is designed to execute assigned script programs 240 received from server 218.

Figure 9:
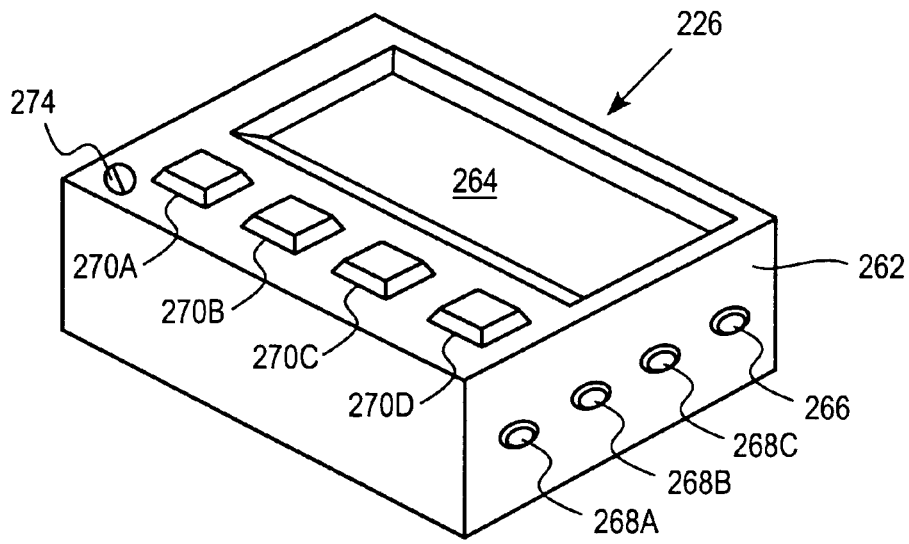
FIG. 9, is a perspective view of a remotely programmable apparatus according to one embodiment of the invention.
Figure 10:
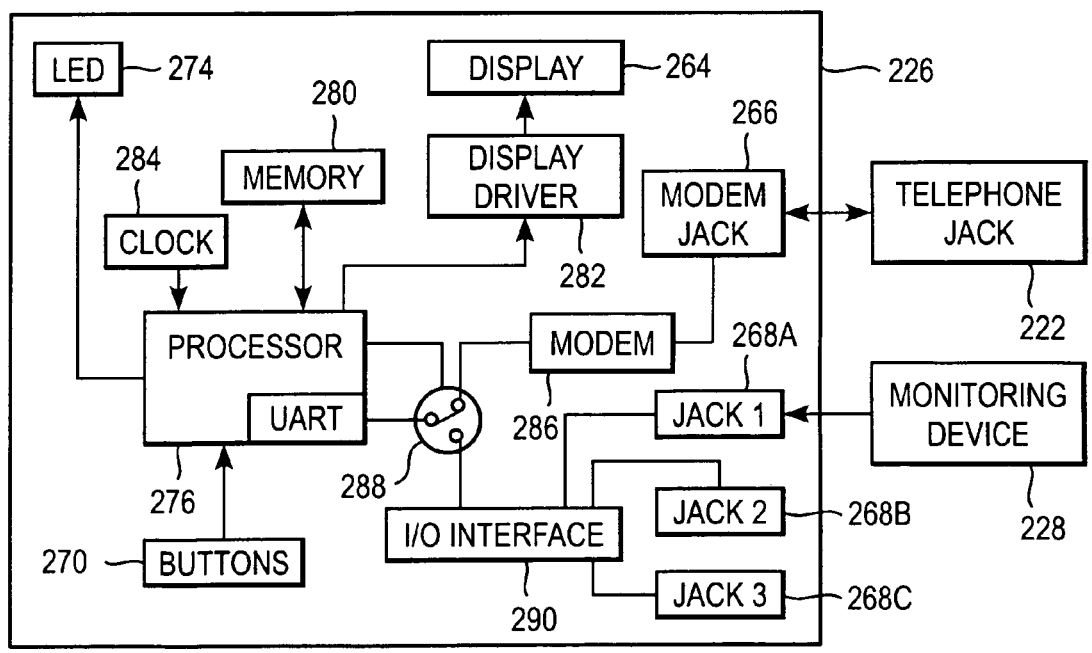
FIG. 10 is a schematic diagram of the components of the apparatus of FIG. 9.

FIGS. 9-10 show an exemplary structure of each remotely programmable apparatus according to one embodiment. For clarity, only remotely programmable apparatus 226 is shown since each remotely programmable apparatus of this embodiment can be substantially identical structure to apparatus 226. Referring to FIG. 9, apparatus 226 includes a housing 262. Housing 262 is sufficiently compact to enable apparatus 226 to be hand-held and carried by a power tool operator. Apparatus 226 also includes a display 264 for displaying queries and prompts to the power tool operator. In one embodiment, display 264 is a liquid crystal display (LCD).

Four user input buttons 270A, 270B, 270C, and 270D are located adjacent display 264. User input buttons 270A-D are for entering in apparatus 226 responses 242 to the queries and prompts. In the preferred embodiment, user input buttons 270A-D are momentary contact push buttons. In alternative embodiments, user input buttons 270A-D may be replaced by switches, keys, a touch sensitive display screen, or any other data input device.

Three monitoring device jacks 268A, 268B, and 268C are located on a surface of housing 262. Device jacks 268A-C are for connecting apparatus 226 to a number of sensors 228. Apparatus 226 also includes a modem jack 266 for connecting apparatus 226 to a telephone jack through a standard connection cord (not shown). Apparatus 226 further includes a visual indicator, such as a light emitting diode (LED) 274. LED 274 is for visually notifying the power tool operator that he or she has unanswered queries stored in apparatus 226.

FIG. 10 is a schematic block diagram illustrating the components of apparatus 226 in greater detail. Apparatus 226 includes a microprocessor 276 and a memory 280 connected to microprocessor 276. Memory 280 is preferably a nonvolatile memory, such as a serial EEPROM. Memory 280 stores script programs 240 received from server 218, measurements 244 received from sensor 228, responses 242 to queries, and the power tool's unique identification code. Microprocessor 276 also includes built-in read only memory (ROM) which stores firmware for controlling the operation of apparatus 226. The firmware includes a script interpreter used by microprocessor 276 to execute script programs 240. The script interpreter interprets script commands which are executed by microprocessor 276. Specific techniques for interpreting and executing script commands in this manner are well known in the art.

Microprocessor 276 is preferably connected to memory 280 using a standard two-wire $I^2C$ interface. Microprocessor 276 is also connected to user input buttons 270, LED 274, a clock 284, and a display driver 282. Clock 284 indicates the current date and time to microprocessor 276. For clarity of illustration, clock 284 is shown as a separate component, but is preferably built into microprocessor 276. Display driver 282 operates under the control of microprocessor 276 to display information on display 264. Microprocessor 276 is preferably a PIC 16C65 processor which includes a universal asynchronous receiver transmitter (UART) 278. UART 278 is for communicating with a modem 286 and a device interface 290. A CMOS switch 288 under the control of microprocessor 276 alternately connects modem 286 and interface 290 to UART 278.

Modem 286 is connected to a telephone jack 222 through modem jack 266. Modem 286 is for exchanging data with server 218 through communication network 224. The data includes script programs 240 which are received from server 218 as well as responses 242 to queries, device measurements 244, script identification codes, and the power tool's unique identification code which modem 286 transmits to server 218. Any suitable modem may be used.

Device interface 290 is connected to device jacks 268A, 268B, and 268C. Device interface 290 is for interfacing with a number of sensors 228, through device jacks 268A-C. Device interface 290 operates under the control of microprocessor 276 to collect measurements 244 from sensors 228 and to output the measurements to microprocessor 276 for storage in memory 280. In one embodiment, interface 290 is a standard RS232 interface. For simplicity of illustration, only one device interface 290 is shown in FIG. 10. However, in alternative embodiments, apparatus 226 may include multiple device interfaces to accommodate sensors 228 which have different connection standards.

Referring again to FIG. 8, server 218 includes a monitoring application 248. Monitoring application 248 is a controlling software application executed by server 218 to perform the various functions described below. Application 248 includes a script generator 250, a script assignor 252, and a report generator 254. Script generator 250 is designed to generate script programs 240 from script information entered through workstation 220. The script information is entered through a script entry screen 256. In the preferred embodiment, script entry screen 256 is implemented as a web page on server 218. Workstation 220 includes a web browser for accessing the web page to enter the script information.

Figure 11:
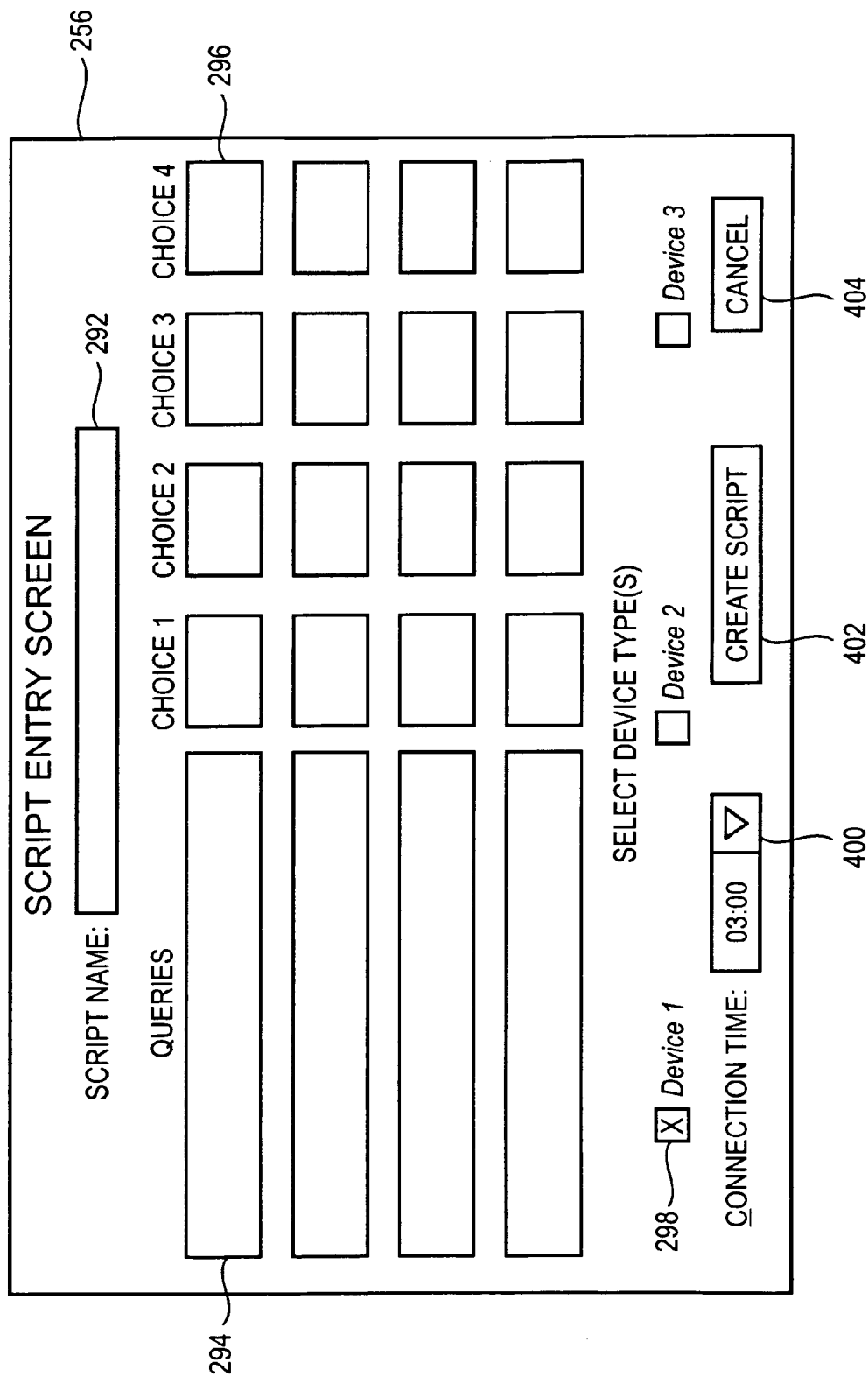
FIG. 11 is a script entry screen according to an embodiment of the invention.

FIG. 11 illustrates one embodiment of a script entry screen 256 as it appears on workstation 220. Screen 256 includes a script name field 292 for specifying the name of a script program to be generated. Screen 256 also includes entry fields 294 for entering a set of queries to be answered by a power tool operator. Each entry field 294 has corresponding response choice fields 296 for entering response choices for the query. Screen 256 further includes check boxes 298 for selecting a desired sensor 228 from which to collect measurements 244.

Screen 256 additionally includes a connection time field 400 for specifying a prescribed connection time at which each apparatus 226 executing the script is to establish a subsequent communication link to server 218. The connection time is preferably selected to be the time at which communication rates are the lowest, such as 3:00 AM. Screen 256 also includes a CREATE SCRIPT button 402 for instructing script generator 250 to generate a script program 240 from the information entered in screen 256. Screen 256 further includes a CANCEL button 404 for canceling the information entered in screen 256.

In one embodiment, each script program 240 created by script generator 250 conforms to the standard file format used on UNIX systems. In the standard file format, each command is listed in the upper case and followed by a colon. Every line in the script program 240 is terminated by a linefeed character {LF}, and only one command is placed on each line. The last character in the script program 240 is a UNIX end of file character {EOF}. Table 1 shows an exemplary listing of script commands used in the preferred embodiment of the invention.

TABLE 1

SCRIPT COMMANDS
Command Description

CLS: {LF}
    Clear the display.
ZAP: {LF}
    Erase from memory the last set of query responses recorded.
LED: b{LF}
    Turn the LED on or off, where b is a binary digit of 0 or 1. An argument of 1 turns on the LED, and an argument of 0 turns off the LED.
DISPLAY: Display the text following the DISPLAY command.
{chars} {LF}
INPUT: Record a button press. The m's represent a button mask
mmmm{LF} pattern for each of the four input buttons. Each m
    contains an "X" for disallowed buttons or an "O" for allowed buttons. For example, INPUT: OXOX{LF} allows the user to press either button #1 or #3.
WAIT: Wait for any one button to be pressed, then continue
{LF} executing the script program.
COLLECT: Collect measurements from the sensor
device{LF}
    specified in the COLLECT command. The user is preferably prompted to connect the specified sensor to the apparatus and press a button to continue.
NUMBER: Assign a script identification code to the script program.
aaaa{LF} The script identification code from the most recently
    executed NUMBER statement is subsequently transmitted to the server along with the query responses and device measurements. The script identification code identifies to the server which script program was most recently executed by the remote apparatus.
DELAY: Wait until time t specified in the DELAY command,
t{LF} usually the prescribed connection time.
CONNECT: Perform a connection routine to establish a
{LF} communication link to the server, transmit the power tool identification code, query responses, device measurements, and script identification code to the server, and receive and store a new script program. When TABLE 1-continued SCRIPT COMMANDS
Command Description the server instructs the apparatus to disconnect, the script interpreter is restarted, allowing the new script program to execute.

The script commands illustrated in Table 1 are representative of one embodiment and are not intended to limit the scope of the invention. After consideration of the ensuing description, it will be apparent to one skilled in the art many other suitable scripting languages and sets of script commands may be used to implement the invention.

The script program 240 includes display commands to display the queries and response choices entered in fields 294 and 296, respectively. The script program 240 also includes input commands to receive responses 242 to the queries. The script program 240 further includes a collect command to collect device measurements 244 from the sensor 228 specified in check boxes 298. The script program 240 also includes commands to establish a subsequent communication link to server 218 at the connection time specified in field 400 FIG. 11. The steps included in the script program 240 are also shown in the flow chart of FIGS. 17A-17B and will be discussed in the operation section below.

Referring again to FIG. 8, script assignor 252 is for assigning script programs 240 to the power tools. Script programs 240 are assigned in accordance with script assignment information entered through workstation 220. The script assignment information is entered through a script assignment screen 257, which is preferably implemented as a web page on server 218.

Figure 12:
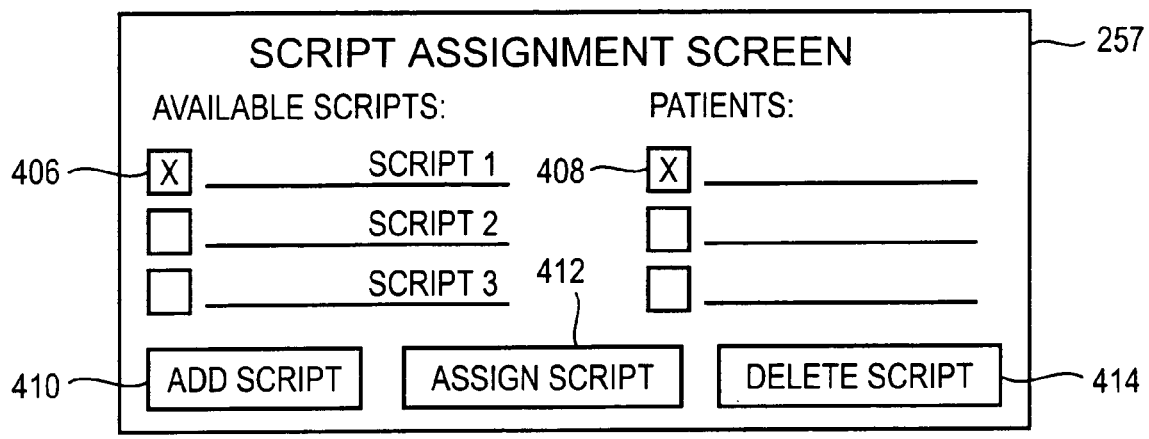
FIG. 12 is a script assignment screen according to an embodiment of the invention.
Figure 13:
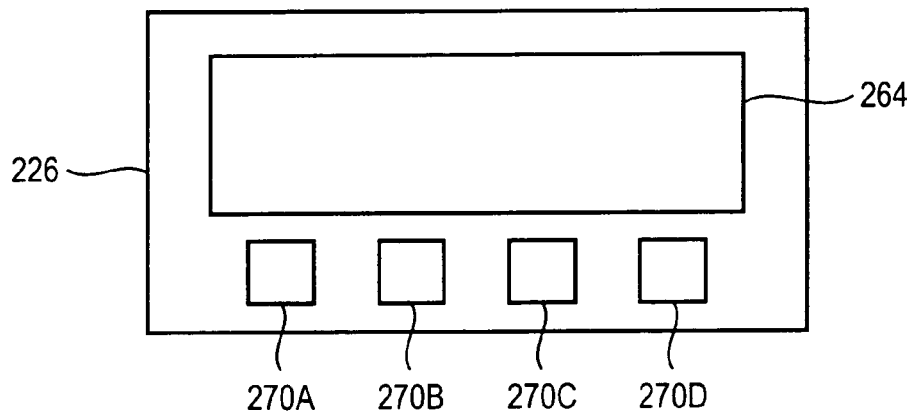
FIG. 13 is a sample query according to an embodiment of the invention.

FIG. 12 illustrates one embodiment of a sample script assignment screen 257 as it appears on workstation 220. Screen 257 includes check boxes 406 for selecting a script program 240 to be assigned, and check boxes 408 for selecting the power tools to which the script program is to be assigned. Screen 257 also includes an ASSIGN SCRIPT button 512 for entering the assignments. When button 412 is pressed, script assignor 252 creates and stores for each power tool selected in check boxes 408 a respective pointer to the script program 240 selected in check boxes 406. Each pointer is stored in the power tool look-up table 246 of database 238. Screen 257 further includes an ADD SCRIPT button 410 for accessing the script entry screen and a DELETE SCRIPT button 414 for deleting a script program 240. In another aspect of this embodiment of the invention, the power tool may be uniquely associated with the purchaser or user of the power tool.

Figure 15:
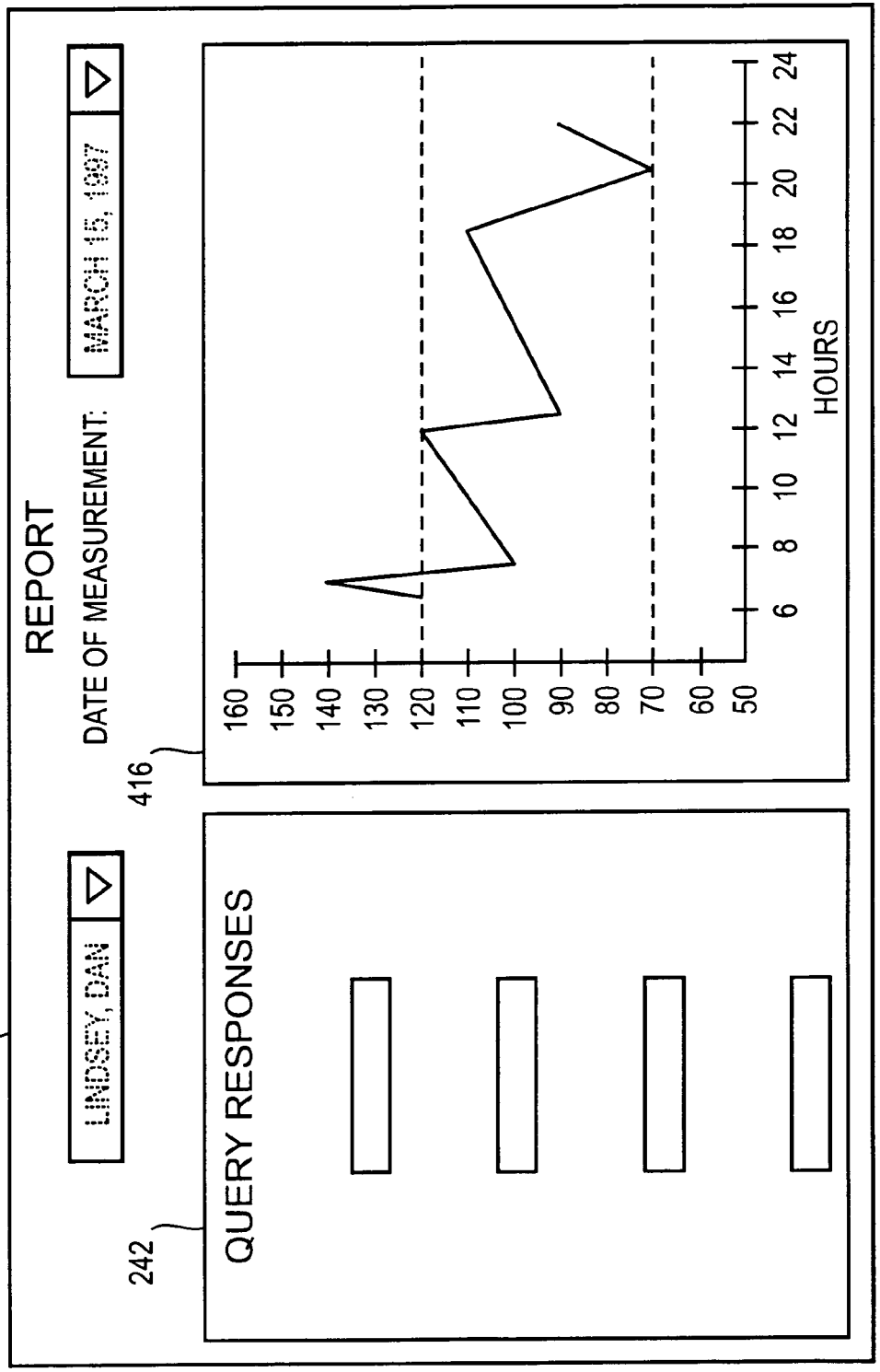
FIG. 15 is a sample report according to an embodiment of the invention.

Referring again to FIG. 8, report generator 254 is designed to generate a power tool report 258 from responses 242 and device measurements 244 received in server 218. Power tool report 258 is displayed on workstation 220. FIG. 15 shows a sample power tool report 258 produced by report generator 254 for a selected power tool. Power tool report 258 includes a graph 416 of the device measurements 244 received from the power tool, as well as a listing of responses 242 received from the power tool operator. Specific techniques for writing a report generator program to display data in this manner are well known in the art.

Figure 16B:
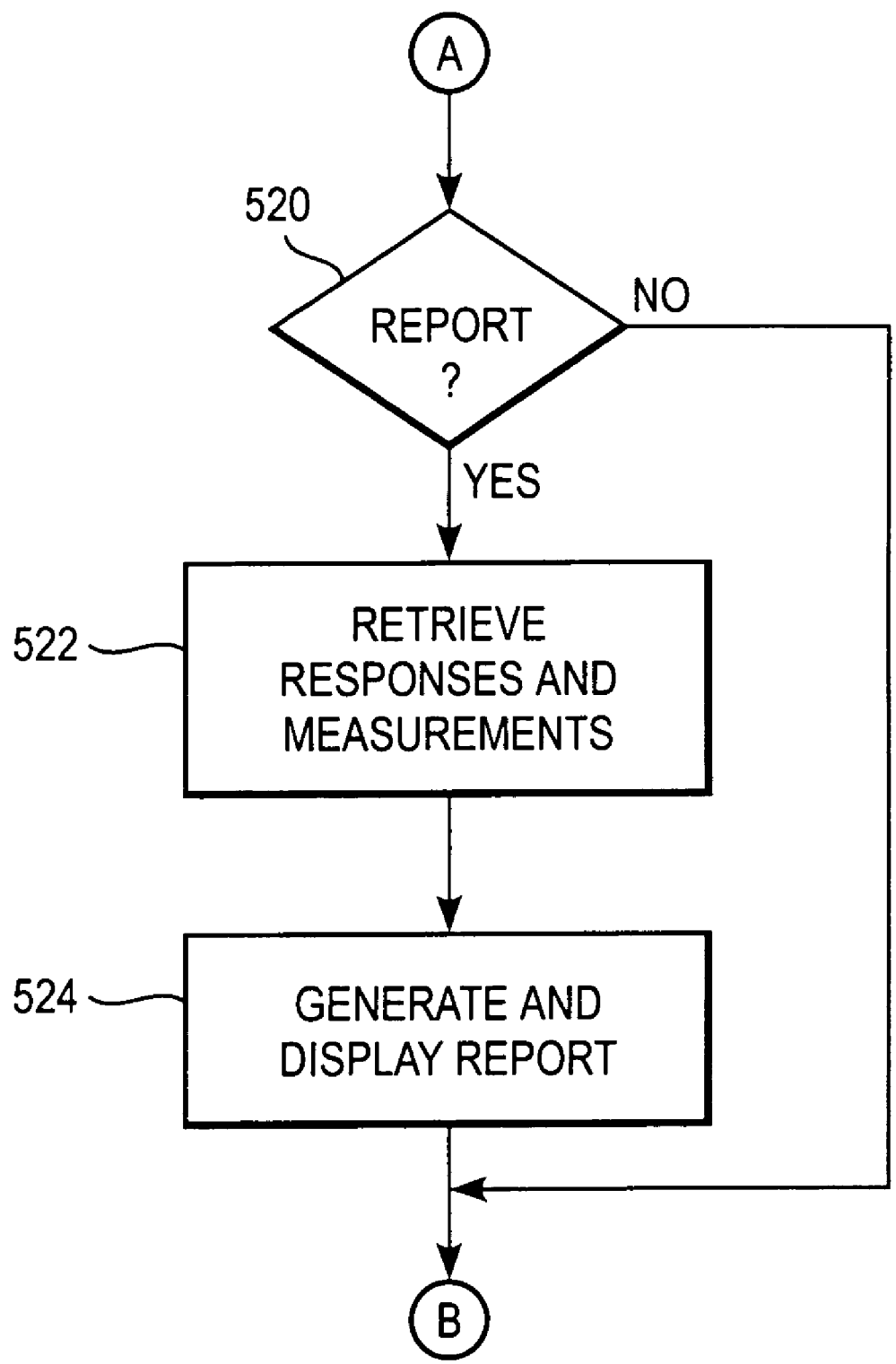
FIG. 16B is continuation of the flow chart of FIG. 16A.

The operation of one embodiment is illustrated in FIGS. 16A-17B. FIG. 16A is a flow chart illustrating steps included in the monitoring application executed by server 218. FIG. 16B is a continuation of the flow chart of FIG. 16A. In step 502, server 218 determines if new script information has been entered through script entry screen 256. If new script information has not been entered, server 218 proceeds to step 506. If new script information has been entered, server 218 proceeds to step 504.

As shown in FIG. 11, the script information includes a set of queries, and for each of the queries, corresponding response choices. The script information also includes a selected monitoring device type from which to collect device measurements 44. The script information further includes a prescribed connection time for each apparatus to establish a subsequent communication link to server 18. The script information is generally entered in server 218 by a service. Of course, any person desiring to communicate with the power tool operator may also be granted access to server 218 to create and assign script programs 40. Further, it is to be understood that system 216 may include any number of remote interfaces for entering script generation and script assignment information in server 218.

In step 504, script generator 250 generates a script program from the information entered in screen 256. The script program is stored in database 238. Steps 502 and 504 are preferably repeated to generate multiple script programs, e.g. a script program for each power tool. Each script program corresponds to a respective one of the sets of queries entered through script entry screen 256. Following step 504, server 218 proceeds to step 506.

In step 506, server 218 determines if new script assignment information has been entered through assignment screen 257. If new script assignment information has not been entered, server 218 proceeds to step 510. If new script assignment information has been entered, server 218 proceeds to step 508. As shown in FIG. 12 the script programs are assigned to each power tool by selecting a script program through check boxes 506, selecting the power tools to whom the selected script program is to be assigned through check boxes 408, and pressing the ASSIGN SCRIPT button 412. When button 412 is pressed, script assignor 252 creates for each power tool selected in check boxes 408 a respective pointer to the script program selected in check boxes 406. In step 508, each pointer is stored in look-up table 246 of database 238. Following step 508, server 218 proceeds to step 510.

In step 510, server 218 determines if any of the apparatuses are remotely connected to the server. Each power tool operator to be monitored is preferably provided with his or her own remotely programmable apparatus which has the power tool's unique identification code stored therein. Each power tool is thus uniquely associated with a respective one of the apparatuses. If none of the apparatuses is connected, server 218 proceeds to step 520.

If an apparatus is connected, server 218 receives from the apparatus the power tool's unique identification code in step 512. In step 514, server 218 receives from the apparatus the query responses 242, device measurements 244, and script identification code recorded during execution of a previously assigned script program. The script identification code identifies to server 218 which script program was executed by the apparatus to record the query responses 242 and device measurements 244. The responses, device measurements, and script identification code are stored in database 238.

In step 516, server 218 uses the power tool identification code to retrieve from table 246 the pointer to the script program assigned to the power tool. Server 218 then retrieves the assigned script program from database 238. In step 518, server 218 transmits the assigned script program to the power tool's remotely programmable apparatus through communication network 224. Following step 518, server 218 proceeds to step 520.

In step 520, server 218 determines if a power tool report request has been received from workstation 220. If no report request has been received, server 218 returns to step 502. If a report request has been received for a selected power tool, server 218 retrieves from database 238 the measurements 244 and query responses 242 last received from the power tool, step 522. In step 524, server 218 generates and displays power tool report 258 on workstation 220. As shown in FIG. 15, report 258 includes the device measurements 244 and query responses 242 last received from the power tool. Following step 524, server 218 returns to step 502.

Figure 17A:
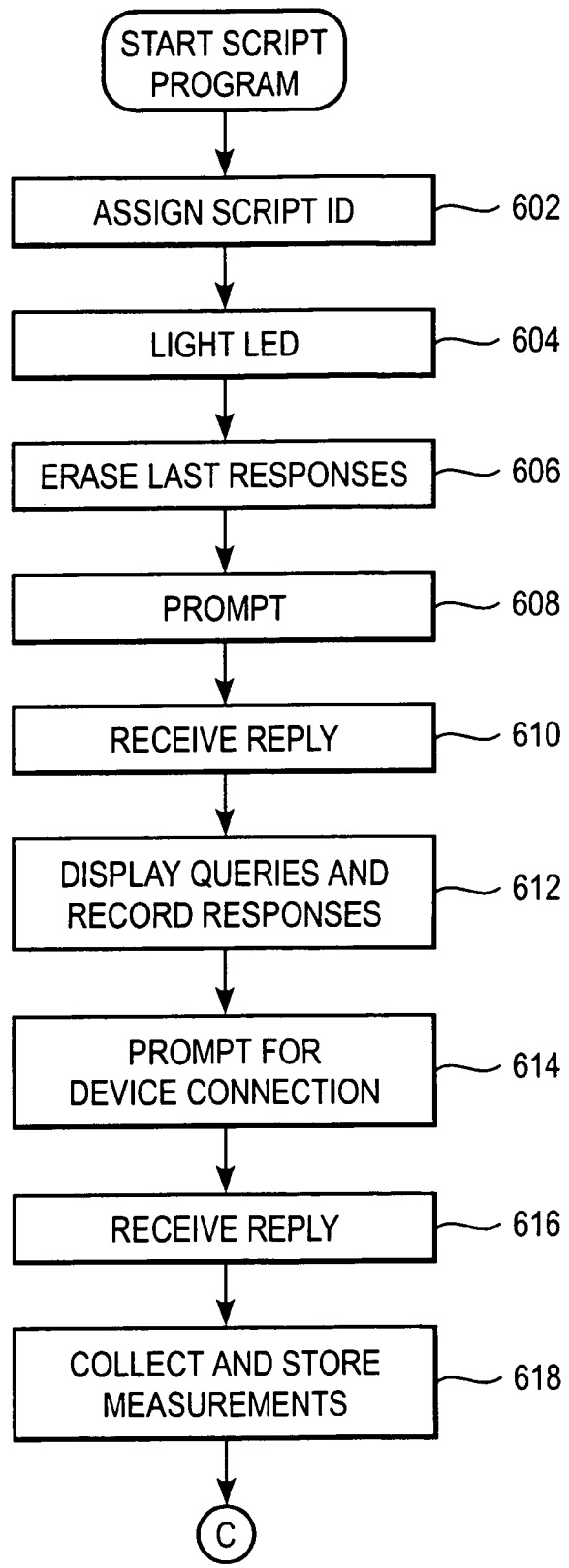
FIG. 17A is a flow chart of a sample script according to one embodiment of the invention.
Figure 17B:
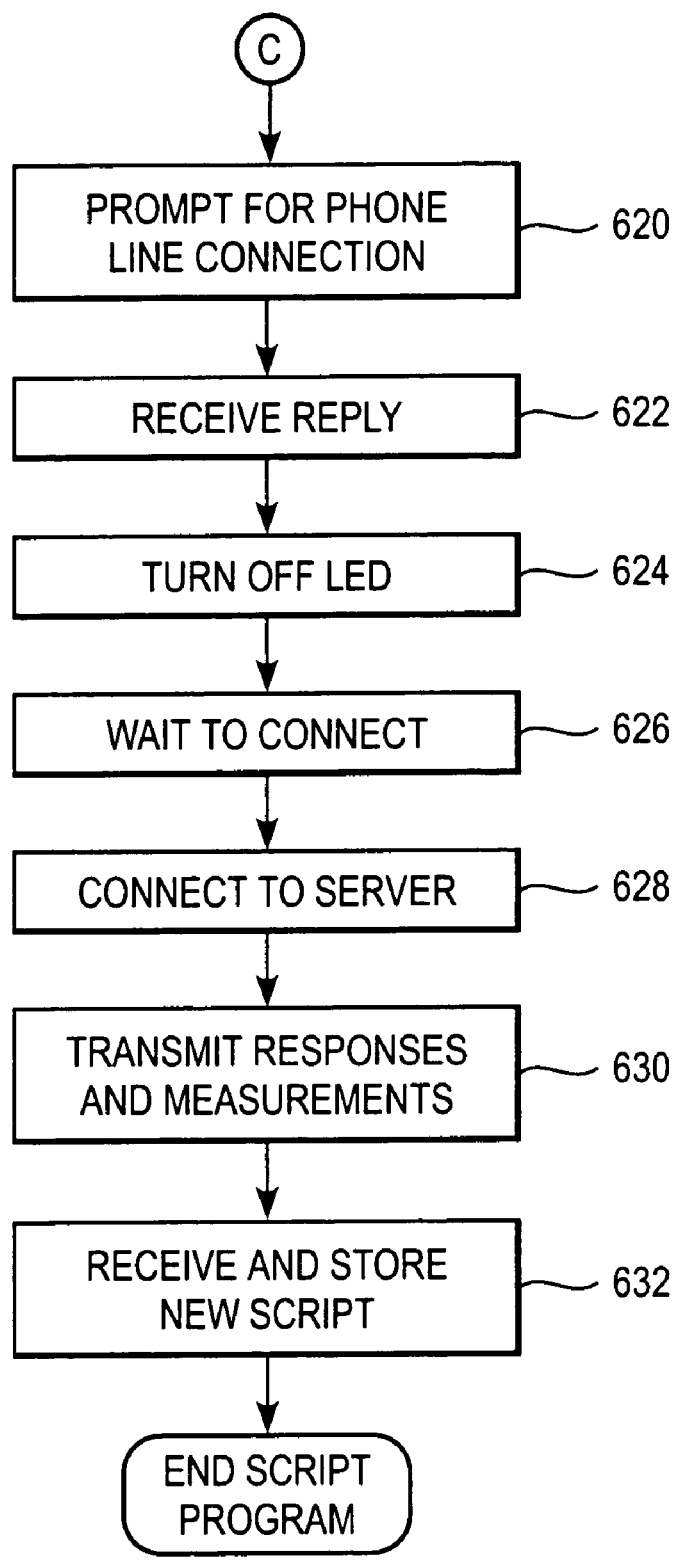
FIG. 17B is a continuation of the flow chart of FIG. 17A.

FIGS. 17A-17B illustrate the steps included in the script program executed by apparatus 226. Before the script program is received, apparatus 226 is initially programmed with the power tool's unique identification code and the script interpreter used by microprocessor 276 to execute the script program. The initial programming may be achieved during manufacture or during an initial connection to server 218. Following initial programming, apparatus 226 receives from server 218 the script program assigned to the power tool associated with apparatus 226. The script program is received by modem 286 through a first communication link and stored in memory 280.

In step 602, microprocessor 276 assigns a script identification code to the script program and stores the script identification code in memory 280. The script identification code is subsequently transmitted to server 218 along with the query responses 242 and device measurements 244 to identify to server 218 which script program was most recently executed by apparatus 226. In step 604, microprocessor 276 lights LED 274 to notify the power tool that he or she has unanswered queries stored in apparatus 226. LED 274 preferably remains lit until the queries are answered by the power tool. In step 606, microprocessor 276 erases from memory 280 the last set of query responses recorded.

In step 608, microprocessor 276 prompts the power tool by displaying on display 264 "ANSWER QUERIES NOW? PRESS ANY BUTTON TO START". In step 610, microprocessor 276 waits until a reply to the prompt is received from the power tool operator. When a reply is received, microprocessor 276 proceeds to step 612. In step 612, microprocessor 276 executes successive display and input commands to display the queries and response choices on display 264 and to receive responses to the queries.

Figure 14:
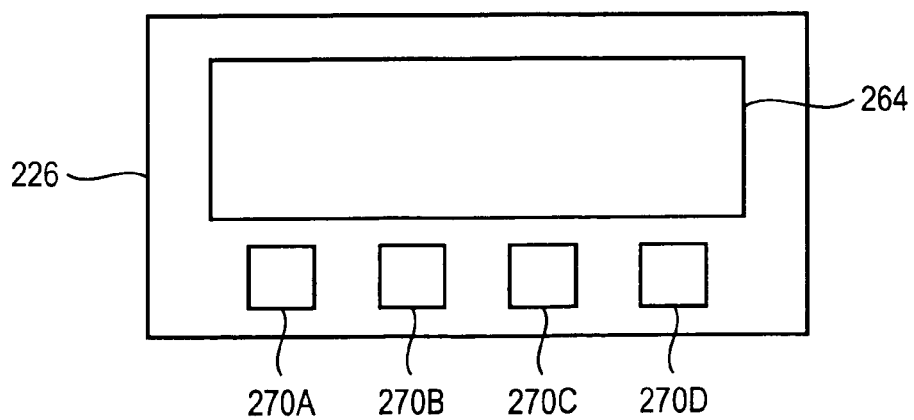
FIG. 14 is a sample prompt according to an embodiment of the invention.

In steps 614-618, microprocessor 276 executes commands to collect device measurements 244 from a selected sensor 228. The script program specifies the selected sensor 228 from which to collect the measurements. In step 614, microprocessor 276 prompts the power tool to connect the selected sensor 228. A sample prompt is shown in FIG. 14. In step 616, microprocessor 276 waits until a reply to the prompt is received from the power tool. When a reply is received, microprocessor 276 proceeds to step 618. Microprocessor 276 also connects UART 278 to interface 290 through switch 288. In step 618, microprocessor 276 collects device measurements 244 from sensor 228 through interface 290 measurements 244 are stored in memory 280.

In step 620, microprocessor 276 prompts the power tool to connect apparatus 226 to telephone jack 222 so that apparatus 226 may connect to server 218 at the prescribed connection time. In step 622, microprocessor 276 waits until a reply to the prompt is received from the power tool. When a reply is received, microprocessor 276 turns off LED 274 in step 624. In step 626, microprocessor 276 waits until it is time to connect to server 218. Microprocessor 276 compares the connection time specified in the script program to the current time output by clock 284. When it is time to connect, microprocessor 276 connects UART 278 to modem 286 through switch 288.

In step 628, microprocessor 276 establishes a subsequent communication link between apparatus 226 and server 218 through modem 286 and communication network 224. If the connection fails for any reason, microprocessor 276 repeats step 628 to get a successful connection. In step 630, microprocessor 276 transmits the device measurements 244, query responses 242, script identification code, and power tool identification code stored in memory 280 to server 218 through the subsequent communication link. In step 632, microprocessor 276 receives through modem 286 a new script program from server 218. The new script program is stored in memory 280 for subsequent execution by microprocessor 276. Following step 632, the script program ends.

It should be understood that all or a portion of the operations and functionality of unit 226 may be performed by power tool 15 by the incorporation of some or all of the above-described components into the power tool 15.

The present invention provides many advantages. For example, the sensors and guidance built into tool provide increased accuracy in measurement fewer mistakes in cutting. Additionally, the present invention increases materials optimization. With the present invention, the user can input descriptions (e.g., length, width, thickness) of the materials he has, and let the system determine optimal cuts to avoid waste. An additional advantage is that step-by-step instructions for the project plan can be built right into the tool or in an associated device. The tool teaches the user step-by-step how to perform its functions and to track progress in each project. Another advantage is that the system may provide added safety by monitoring heat, vibrations and other parameters. The tool can monitor safety and provide feedback to the end-user to improve safety compliance. The tool can also improve security. By sensing the identity of the end-user, the system can prevent theft. Also, by logging into a server, the system can track usage and location. Further, the system can improve compliance. For industrial and business applications, the system can record use and misuse patterns to ensure compliance with safety procedures and provide documentation for worker's compensation or disability claims in the event of an accident. The system can also aid in marketing by interacting with the end user on the site of a job or project. Valuable marketing data can be gathered to support product improvement and cross marketing opportunities. Additionally, the system can also improve customer support by collecting data from tools while they are being used. An additional advantage of the system is that it can improve the productivity and effectiveness of customer support functions.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

I claim:

1. A power tool system comprising:
   a programmable microprocessor;
   at least one input mechanism;
   a memory having instructions executable by said programmable microprocessor;
   a display;
   at least one power tool having at least one sensor operable for monitoring a parameter associated with operation of the power tool and for producing digitally encoded signals representative of the monitored parameter;
   a communications device connectable in signal communication with both the programmable microprocessor and the at least one sensor; and
   wherein said executable program instructions for the programmable microprocessor (i) cause instructions stored in the memory to be presented to the user on the display, (ii) collect data from a user interaction with the at least one input mechanism in response to the display and stores data in memory, (iii) collect data from the at least one sensor and stores the data in memory, (iv) transmit test results and other data to a remotely located server over a communication network, (v) receive from the server instructions stored on the server for transmission to the programmable microprocessor, and (vi) store instructions in the memory.

2. The power tool system of claim 1, wherein the programmable microprocessor is located in a programmable microprocessor device or integrated into the power tool.

3. The power tool system of claim 1, wherein the communications device is provided within a communications unit and a central processing device of the communications device causes the signals representative of the monitored parameter to be stored in a memory circuit of the communications unit; and wherein the communications unit further includes a the communications device for transmitting the stored digitally encoded signals representative of the monitored parameter to a remotely located service provider.

4. The power tool system of claim 3, wherein the system is configured to transmit a message from the service provider to the display.

5. The power tool system of claim 4, wherein the message includes step-by-step instructions, tool positioning for an upcoming cut, a laser guide cut length, a record of successful cuts, a list of upcoming cuts, project design, scaling factors, a materials list, a cut list, wood or materials type, or equipment information.

6. The power tool system of claim 4, wherein the message is educational or provides feedback.

7. The power tool system of claim 6, wherein the programmable microprocessor device comprises a compact video game.

8. The power tool system of claim 3, further comprising a clearinghouse facility for receiving the signals supplied via the communications device of the communications unit, the clearinghouse facility being remotely located from the communications device and including a server having a digital signal processor for converting the digitally encoded signal supplied via the communications device of the communications device into a report that provides information relating to the parameter monitored by at least one sensor.

9. The power tool system of claim 1, wherein the at least one sensor is adapted to measure heat, vibration, moisture, room temperature, location, direction, user identification, power, torque, motor jam, length and time of usage, cut distance, length of cut, equipment manufacturer information, equipment identification, or service record.

10. The power tool system of claim 2, wherein the display is located in the programmable microprocessor device or integrated into the power tool.

11. The power tool system of claim 8, wherein the program instructions included in the memory of the programmable microprocessor cause the programmable microprocessor to display one or more menus on the display and further operation of one or more switches and allows a user of the power tool system to control the operation of the programmable microprocessor and the communications unit, the operation controlled by the user with the one or more switches including the processing of the digitally encoded signals representative of the monitored parameter, the transmission of the digitally encoded signals from the communications device to the programmable microprocessor and the display of information on the display.

12. The power tool system of claim 11, wherein the one or more menus displayed on the display and further operation of one or more switches allows the user of the power tool system to generate graphic and alphanumeric displays on the display alphanumeric and graphic displays being representative of the signals that are representative of the monitored parameter and stored in the memory circuit of the communications unit.

13. The power tool system of claim 2, wherein the microprocessor device further comprises a receptacle for receiving a program cartridge that includes a memory circuit having stored therein program instructions for controlling the operation of the programmable microprocessor unit.

14. The power tool system of claim 13, wherein the program cartridge adapts the microprocessor device for operation with at least one power tool.

15. The power tool system of claim 13, wherein the program cartridge adapts the power tool to operate in the power tool system.

16. The power tool system of claim 15, wherein the adaptation occurs by downloading program instructions from a network server located at a clearinghouse facility.

17. The power tool system of claim 16, wherein the downloaded program instructions reconfigure the operation of the at least one power tool.

18. The power tool system of claim 16, wherein the program instructions are selected by a user of the power tool system from a website, or by a service provider.

19. The power tool system of claim 18, wherein the service provider is an authorized professional in customer service for the tool manufacturer, a retailer, or third party program developer of project plans and designs.

20. The power tool system of claim 8, wherein the signals are received by the remote clearinghouse via telephone landline, cell phone, or via RF.

21. The power tool system of claim 8, wherein the report is standardized and sent to the service provider.

22. The power tool system of claim 21, wherein the report includes statistical information.

23. The power tool system of claim 8, wherein the system is configured to transmit a message from the clearinghouse facility to the display.

24. The power tool system of claim 23, wherein the message includes step-by-step instructions, tool positioning for an upcoming cut, a laser guide cut length, a record of successful cuts, a list of upcoming cuts, project design, scaling factors, a materials list, a cut list, wood or materials type, or equipment information.

25. The power tool system of claim 23, wherein the message is educational or provides feedback.

26. The power tool system of claim 8, wherein the system is configured to transmit a message from the clearinghouse to the display.

27. The power tool system of claim 26, wherein the message is transmitted automatically.

28. The power tool system of claim 11, wherein a user of the programmable microprocessor answers survey questions with one or more of switches.

29. The power tool system of claim 11, wherein the user inputs data associated with the user's materials and the system determines the optimal cuts.

30. The power tool system of claim 11, wherein the user inputs equipment and materials data and in response settings are sent from the clearinghouse facility to the tool via the data management unit.

31. The power tool system of claim 1, wherein the power tool is a drill, saw, sander, grinder, router, or joiner.

32. A method of using a modular microprocessor power tool system comprising: (a) at a site employing a power tool,
   (i) using stored program instructions when executed by the modular microprocessor generates power tool related information on at least one display; (ii) collecting power tool related data using a programmable microprocessor;
   (b) connecting at least one remotely located computing facility including at least one central server for communication with a communications device at the power tool site; and
   (c) providing power tool data to at least one service provider computer remotely located from and in signal communication with the central server, wherein hardware and software of the central server are configured to receive and store power tool-15 related data from a power tool site that can be viewed or retrieved by an authorized user from the remotely located service provider computer.

33. The method of claim 32, wherein the central server receives messages from the remotely located service provider computer and transmits the messages to the power tool site.

34. The method of claim 33, wherein the message includes step-by-step instructions, tool positioning for an upcoming cut, a laser guide cut length, a record of successful cuts, a list of upcoming cuts, project design, scaling factors, a materials list, a cut list, wood or materials type, or equipment information.

35. The method of claim 33, wherein the message is educational or provides feedback.

36. The method of claim 32, wherein the power tool data is generated from at least one sensor associated with the power tool.

37. The method of claim 35, wherein the power tool comprises a plurality of sensors.

38. The method of claim 37, wherein the sensors measure heat, vibration, moisture, room temperature, location, direction, user identification, power, torque, motor jam, length and time of usage, cut distance, length of cut, equipment manufacturer information, equipment identification, or service record.

39. The method of claim 32, further comprising displaying one or more menus on a display of a programmable microprocessor device in signal connection with the communications device, the microprocessor device having one or more switches allowing a user of the power tool system to control the operation of the programmable microprocessor device and the communications device.

40. The method of claim 32, further comprising downloading program instructions from the central server to the data management unit.

41. The method of claim 40, wherein the downloaded program instructions reconfigure the operation of the power tool.

42. The method of claim 40, wherein the downloaded program instructions are selected by a user of the power tool system from a website, or by the service provider.

43. The method of claim 33, further comprising the user inputting equipment and materials data and in response instructions are sent from a clearinghouse facility to the programmable microprocessor device via the communications unit.

* * * * *